United States Patent
Johannes et al.

(12) 
(10) Patent No.: US 12,268,627 B2
(45) Date of Patent: Apr. 8, 2025

(54) FLUID COLLECTION ASSEMBLIES INCLUDING AT LEAST ONE SECUREMENT BODY

(71) Applicant: PureWick Corporation, El Cajon, CA (US)

(72) Inventors: Ashley Marie Johannes, Statham, GA (US); Shahab Siddiqui, Lawrenceville, GA (US); Kathleen Davis, Atlanta, GA (US)

(73) Assignee: PureWick Corporation, Covington, GA (US)

( * ) Notice: Subject to any disclaimer, the term of this patent is extended or adjusted under 35 U.S.C. 154(b) by 6 days.

(21) Appl. No.: 17/646,771

(22) Filed: Jan. 3, 2022

(65) Prior Publication Data
US 2022/0211536 A1 Jul. 7, 2022

Related U.S. Application Data

(60) Provisional application No. 63/134,450, filed on Jan. 6, 2021.

(51) Int. Cl.
*A61F 5/451* (2006.01)
*A61F 5/44* (2006.01)

(52) U.S. Cl.
CPC ............ *A61F 5/451* (2013.01); *A61F 5/4404* (2013.01)

(58) Field of Classification Search
CPC .......... A61F 5/441; A61F 5/442; A61F 5/443; A61F 5/451; A61F 5/4408; A61F 5/44;
(Continued)

(56) References Cited

U.S. PATENT DOCUMENTS 737,443 A 8/1903 Mooers
1,032,841 A 7/1912 Koenig
(Continued)

FOREIGN PATENT DOCUMENTS

AU 2018216821 A1 8/2019
AU 2021299304 A1 2/2023
(Continued)

OTHER PUBLICATIONS

US 9,908,683 B2, 03/2018, Sandhausen et al. (withdrawn)
(Continued)

*Primary Examiner* — Ariana Zimbouski
*Assistant Examiner* — Timothy L Flynn
(74) *Attorney, Agent, or Firm* — Dorsey & Whitney LLP

(57) ABSTRACT

Embodiments disclosed herein include fluid collection assemblies with at least one securement body. In an embodiment, a fluid collection assembly is disclosed. The fluid collection assembly includes a fluid impermeable barrier at least defining a chamber, at least one opening, and a fluid outlet. The fluid collection assembly also includes at least one porous material disposed in the chamber and at least one securement body configured to limit movement of the fluid collection assembly relative to a region about a urethral opening of a patient. The at least one securement body includes at least one of a plurality of fibers exhibiting an average lateral dimension of about 5 μm or less, a plurality of suction cups, or at least one friction material exhibiting a coefficient of static friction that is greater than at least a portion of the at least one porous material.

12 Claims, 8 Drawing Sheets

(58) Field of Classification Search
CPC ........ A61F 5/455; A61F 5/4404; A61F 13/15; A61F 13/56; A61F 13/62; A61F 13/64; A61F 13/66; A61F 13/581; A61F 13/82; A61F 2013/16; A61F 2013/51097; A61F 2013/5694; C09J 2301/31

See application file for complete search history.

(56) References Cited

U.S. PATENT DOCUMENTS

| | | |
|---|---|---|
| 1,178,644 A | 4/1916 | Johnson |
| 1,387,726 A | 8/1921 | Karge |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,571,357 A | 10/1951 | Charles |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | McGuire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,865,109 A | 2/1975 | Elmore et al. |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,223,677 A | 9/1980 | Anderson |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,403,991 A | 9/1983 | Hill |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | McNeil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,784,654 A | 11/1988 | Beecher |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |

(56) References Cited

U.S. PATENT DOCUMENTS

| | | |
|---|---|---|
| 4,889,533 A | 12/1989 | Beecher |
| 4,890,691 A | 1/1990 | Ching-ho |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,955,922 A | 9/1990 | Terauchi |
| 4,957,487 A | 9/1990 | Gerow |
| 4,965,460 A | 10/1990 | Tanaka et al. |
| 4,986,823 A | 1/1991 | Anderson et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,057,092 A | 10/1991 | Webster |
| 5,058,088 A | 10/1991 | Haas et al. |
| 5,071,347 A | 12/1991 | McGuire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,203,699 A | 4/1993 | McGuire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,282,795 A | 2/1994 | Finney |
| 5,294,983 A | 3/1994 | Ersoz et al. |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,459 A | 7/1994 | Lavon et al. |
| 5,340,840 A | 8/1994 | Park et al. |
| 5,382,244 A | 1/1995 | Telang |
| 5,409,014 A | 4/1995 | Napoli et al. |
| 5,411,495 A | 5/1995 | Willingham |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,700,254 A | 12/1997 | Mcdowall et al. |
| 5,701,612 A | 12/1997 | Daneshvar |
| 5,705,777 A | 1/1998 | Flanigan et al. |
| 5,752,944 A | 5/1998 | Dann et al. |
| 5,763,333 A | 6/1998 | Suzuki et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,876,393 A | 3/1999 | Ahr et al. |
| 5,887,291 A | 3/1999 | Bellizzi |
| 5,891,125 A | 4/1999 | Plumley |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,007,526 A | 12/1999 | Passalaqua et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,446,454 B1 | 9/2002 | Lee et al. |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |

(56) References Cited

U.S. PATENT DOCUMENTS

| | | | |
|---|---|---|---|
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 * | 10/2010 | Lindsay ............... A61F 13/58 604/389 |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 * | 8/2016 | Roy ....................... A41C 5/005 |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |

(56) References Cited

U.S. PATENT DOCUMENTS

| | | |
|---|---|---|
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | McGirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Mllarreal |
| 10,407,222 B2 | 9/2019 | Allen |
| 10,478,356 B2 | 11/2019 | Griffin |
| 10,500,108 B1 | 12/2019 | Maschino et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,226,376 B2 | 1/2022 | Yamauchi et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,925,575 B2 | 3/2024 | Newton |
| 11,938,053 B2 | 3/2024 | Austermann et al. |
| 11,944,740 B2 | 4/2024 | Hughett et al. |
| 12,023,457 B2 | 7/2024 | Mann et al. |
| 12,042,422 B2 | 7/2024 | Davis et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |

(56) References Cited

U.S. PATENT DOCUMENTS

| | | |
|---|---|---|
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Mrginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1* | 12/2013 | Aizenberg .......... B81C 1/00349 428/116 |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |

(56) References Cited

U.S. PATENT DOCUMENTS

| | | |
|---|---|---|
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1* | 9/2019 | Johannes ................. A61F 5/445 |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-Schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Mllarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1 | 10/2021 | Jiang |

(56) References Cited

U.S. PATENT DOCUMENTS

| | | |
|---|---|---|
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0052238 A1 | 2/2023 | Oluwasogo |
| 2023/0062944 A1 | 3/2023 | Vollenberg et al. |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Mn et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065881 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |

FOREIGN PATENT DOCUMENTS

| | | |
|---|---|---|
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1434693 A | 8/2003 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 205849719 U | 1/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 79818 C | 10/1893 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 202015104597 U1 | 7/2016 |
| DE | 102020121462 B3 | 1/2022 |
| DK | 9600118 | 11/1996 |
| EP | 0032138 A2 | 7/1981 |
| EP | 0068712 A1 | 1/1983 |

(56) References Cited

FOREIGN PATENT DOCUMENTS

| | | |
|---|---|---|
| EP | 0140470 A1 | 5/1985 |
| EP | 066070 B1 | 9/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| EP | 3569205 B1 | 6/2023 |
| EP | 4382082 A2 | 6/2024 |
| GB | 871820 A | 7/1961 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S498638 U | 1/1974 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H04060220 U | 5/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003126242 A | 5/2003 |
| JP | 2003180722 A | 7/2003 |
| JP | 2003528691 A | 9/2003 |
| JP | 2004057578 A | 2/2004 |
| JP | 2004130056 A | 4/2004 |
| JP | 2004267530 A | 9/2004 |
| JP | 2005052219 A | 3/2005 |
| JP | 2005066011 A | 3/2005 |
| JP | 2005066325 A | 3/2005 |
| JP | 2005102978 A | 4/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2010504150 A | 2/2010 |
| JP | 2010081981 A | 4/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2016521191 A | 7/2016 |
| JP | 2017014698 A | 1/2017 |
| JP | 2019525811 A | 9/2019 |
| JP | 2019170942 A | 10/2019 |
| JP | 2019533492 A | 11/2019 |
| JP | 2021120686 A | 8/2021 |
| JP | 2021522009 A | 8/2021 |
| JP | 2021522013 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| SE | 505542 C2 | 9/1997 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |

(56) References Cited

FOREIGN PATENT DOCUMENTS

| | | | |
|---|---|---|---|
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |

(56) References Cited

FOREIGN PATENT DOCUMENTS

| | | | |
|---|---|---|---|
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022031943 | A1 | 2/2022 |
| WO | 2022035745 | A1 | 2/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022222030 | A1 | 10/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023023777 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023191764 | A1 | 10/2023 |
| WO | 2023244238 | A1 | 12/2023 |
| WO | 2024058788 | A1 | 3/2024 |

OTHER PUBLICATIONS

International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
Non-Final Office Action for U.S. Appl. No. 17/501,591 mailed Apr. 25, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/662,700 mailed Jul. 22, 2022.
Non-Final Office Action for U.S. Appl. No. 29/741,751 mailed Jan. 18, 2022.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 17/662,700 mailed Jan. 30, 2023.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/904,868 mailed Mar. 10, 2022.

(56) References Cited

OTHER PUBLICATIONS

Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/451,345 mailed May 3, 2023.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2020/057562 mailed Jan. 27, 2021.
International Search Report and Written Opinion from International Application No. PCT/US2021/026607 mailed Jul. 29, 2021.
International Search Report and Written Opinion from International Application No. PCT/US2021/039866 mailed Oct. 7, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/044107 mailed Dec. 23, 2022.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/904,868 mailed Mar. 15, 2023.
Non-Final Office Action for U.S. Appl. No. 16/905,400 mailed Apr. 27, 2022.
Non-Final Office Action for U.S. Appl. No. 17/051,550 mailed Dec. 15, 2022.
Non-Final Office Action for U.S. Appl. No. 17/051,585 mailed Mar. 29, 2023.
Non-Final Office Action for U.S. Appl. No. 17/179,116 mailed Mar. 24, 2023.

(56) References Cited

OTHER PUBLICATIONS

Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,354 mailed May 3, 2023.
Non-Final Office Action for U.S. Appl. No. 17/453,260 mailed Mar. 14, 2023.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Mar. 4, 2022.
Notice of Allowance for U.S. Appl. No. 17/330,657 mailed Mar. 16, 2022.
Notice of Allowance for U.S. Appl. No. 17/461,036 mailed Feb. 22, 2023.
Notice of Allowance for U.S. Appl. No. 17/461,036 mailed Oct. 6, 2022.
Notice of Allowance for U.S. Appl. No. 17/662,700 mailed Mar. 28, 2023.
Notice of Allowance for U.S. Appl. No. 17/663,046 mailed Jan. 30, 2023.
Notice of Allowance for U.S. Appl. No. 29/741,751 mailed Jun. 9, 2022.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/646,771 mailed Apr. 6, 2023.
Text Messages to Lorena Eckert Re Prototype PureWick Holder dated Apr. 16, 2022.
U.S. Application No. 15/384, 196 filed Dec. 19, 2016.
U.S. Appl. No. 17/394,055, filed Aug. 4, 2021.
U.S. Appl. No. 17/597,408, filed Jan. 5, 2022.
U.S. Appl. No. 17/597,673, filed Jan. 18, 2022.
U.S. Appl. No. 17/631,619, filed Jan. 31, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152 filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163 filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121 filed Mar. 21, 2023.
U.S. Appl. No. 18/247,986, filed Apr. 5, 2023.
U.S. Appl. No. 18/299,788, filed Apr. 13, 2023.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/094,646, filed Oct. 21, 2020.
U.S. Appl. No. 63/138,878, filed Jan. 19, 2021.
U.S. Appl. No. 63/191,558, filed May 21, 2021.
U.S. Appl. No. 63/192,289, filed May 24, 2021.
U.S. Appl. No. 63/208,262, filed Jun. 8, 2021.
U.S. Appl. No. 63/230,897, filed Aug. 9, 2021.
U.S. Appl. No. 63/241,328, filed Sep. 7, 2021.
U.S. Appl. No. 63/299,208, filed Jan. 13, 2022.
U.S. Appl. No. 63/308,190, filed Feb. 9, 2022.
*PureWick Corporation* v. *Sage Products, LLC* Transcripts vol. 5, Apr. 1, 2022, 72 pages.
*PureWick Corporation* v. *Sage Products, LLC* Transcripts vol. 1, Mar. 28, 2022, 99 pages.
*PureWick Corporation* v. *Sage Products, LLC* Transcripts vol. 2, Mar. 29, 2022, 106 pages.
*PureWick Corporation* v. *Sage Products, LLC* Transcripts vol. 3, Mar. 30, 2022, 115 pages.
*PureWick Corporation* v. *Sage Products, LLC* Transcripts vol. 4, Mar. 31, 2022, 117 pages.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali, "Sustainability Assessment: Seventh Generation Diapers versus gDiapers", The University of Vermont, Dec. 6, 2011, pp. 1-31.

(56) References Cited

OTHER PUBLICATIONS

Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Parness, et al., "A microfabricated wedge-shaped adhesive array displaying gecko-like dynamic adhesion, directionality", J.R. Soc. Interface, 2009, pp. 1223-1232.
Pieper, et al., "An external urine-collection device for women: A clinical trial", Journal of ER Nursing, vol. 20, No. 2, Mar./Apr. 1993, pp. 51-55.
Tsipenyuk, et al., "Use of biomimetic hexagonal surface texture in friction against lubricated skin", Journal of The Royal Society—Interface, 2014, pp. 1-6.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021, 3 pages.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.

(56) References Cited

OTHER PUBLICATIONS

International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 17/088,272 mailed Aug. 5, 2021.
Notice of Allowance for U.S. Appl. No. 17/088,272 mailed Nov. 24, 2021.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.

(56) References Cited

OTHER PUBLICATIONS

Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/433,773, filed Apr. 3, 2020.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/614,173, filed Nov. 24, 2021.
U.S. Appl. No. 17/645,821, filed Dec. 23, 2021.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.

(56) References Cited

OTHER PUBLICATIONS

U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.

"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Step by Step How Ur24 WorksHome", http://medicalpatentur24.com, Aug. 30, 2017, 4 pages.
"Underwear that absorbs your period", Thinx!, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister, "Retracted Penis Pouch by Hollister", Vitality Medical. com, 6 pages.
Macaulay, et al., "A Noninvasive Continence Management System: Development and Evaluation of a Novel Toileting Device for Women", The Wound, Ostomy and Continence Nurses Society, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
Advisory Action for U.S. Appl. No. 16/478,180 mailed Sep. 7, 2023.
Advisory Action for U.S. Appl. No. 17/051,550 mailed Sep. 8, 2023.
Advisory Action for U.S. Appl. No. 17/444,792 mailed Aug. 25, 2023.
Final Office Action for U.S. Appl. No. 16/369,676 mailed Aug. 31, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/653,137 mailed Sep. 21, 2023.
Final Office Action for U.S. Appl. No. 17/655,464 mailed Sep. 1, 2023.
International Search Report and Written Opinion from International Application No. PCT/US2022/043818 mailed Mar. 24, 2023.
International Search Report and Written Opinion from International Application No. PCT/US2022/044208 mailed May 8, 2023.

(56) References Cited

OTHER PUBLICATIONS

International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
Non-Final Office Action for U.S. Appl. No. 17/051,399 mailed Aug. 18, 2023.
Non-Final Office Action for U.S. Appl. No. 17/326,980 mailed Jul. 11, 2023.
Non-Final Office Action for U.S. Appl. No. 17/446,654 mailed Sep. 8, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 18/139,523 mailed Aug. 17, 2023.
Non-Final Office Action for U.S. Appl. No. 18/140,751 mailed Sep. 14, 2023.
Notice of Allowance for U.S. Appl. No. 16/245,726 mailed Jul. 6, 2023.
Notice of Allowance for U.S. Appl. No. 17/051,554 mailed Jul. 6, 2023.
Notice of Allowance for U.S. Appl. No. 17/461,036 mailed Jun. 30, 2023.
Notice of Allowance for U.S. Appl. No. 17/662,700 mailed Jul. 28, 2023.
Notice of Allowance for U.S. Appl. No. 18/299,788 mailed Jul. 24, 2023.
Restriction Requirement for U.S. Appl. No. 17/051,600 mailed Sep. 21, 2023.
Restriction Requirement for U.S. Appl. No. 17/645,821 mailed Jul. 12, 2023.
Restriction Requirement for U.S. Appl. No. 17/657,474 mailed Jun. 30, 2023.
U.S. Appl. No. 17/664,487, filed May 23, 2022.
U.S. Appl. No. 18/259,626, filed Jun. 28, 2023.
U.S. Appl. No. 18/260,122 filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/548,152, filed Aug. 28, 2023.
U.S. Appl. No. 18/549,387, filed Sep. 7, 2023.
U.S. Appl. No. 18/553,625, filed Oct. 2, 2023.
U.S. Appl. No. 63/150,640, filed Feb. 18, 2021.
Merriam-Webster Dictionary, , "Embed Definition & Meaning", https://www.merriam-webster.com/dictionary/ embed last accessed Aug. 3, 2023, 2003.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/904,868 mailed Jan. 2, 2024.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/179,116 mailed Oct. 31, 2023.
Final Office Action for U.S. Appl. No. 17/446,654 mailed Jan. 31, 2024.
Final Office Action for U.S. Appl. No. 17/450,864 mailed Dec. 28, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
Issue Notification for U.S. Appl. No. 16/245,726 mailed Oct. 18, 2023.
Issue Notification for U.S. Appl. No. 17/051,554 mailed Mar. 6, 2024.

(56) References Cited

OTHER PUBLICATIONS

Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,145 mailed Nov. 2, 2023.
Non-Final Office Action for U.S. Appl. No. 16/478,180 mailed Nov. 7, 2023.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/444,792 mailed Nov. 17, 2023.
Non-Final Office Action for U.S. Appl. No. 17/446,256 mailed Feb. 13, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/451,345 mailed Jan. 17, 2024.
Non-Final Office Action for U.S. Appl. No. 17/453,560 mailed Oct. 16, 2023.
Non-Final Office Action for U.S. Appl. No. 17/645,821 mailed Oct. 25, 2023.
Non-Final Office Action for U.S. Appl. No. 17/653,137 mailed Jan. 18, 2024.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/140,163 mailed Nov. 9, 2023.
Non-Final Office Action for U.S. Appl. No. 18/198,464 mailed Dec. 7, 2023.
Notice of Allowance for U.S. Appl. No. 16/369,676 mailed Nov. 14, 2023.
Notice of Allowance for U.S. Appl. No. 17/051,550 mailed Feb. 7, 2024.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/657,474 mailed Mar. 5, 2024.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 18/299,788 mailed Nov. 6, 2023.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/451,719, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/549,658, filed Sep. 8, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 63/596,012, filed Nov. 3, 2023.
U.S. Appl. No. 63/608,553, filed Dec. 11, 2023.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/444,792 mailed Jul. 8, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/645,821 mailed Jul. 2, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Corrected Notice of Allowability for U.S. Appl. No. 17/501,591 mailed Aug. 9, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/653,137 mailed Aug. 7, 2024.
Final Office Action for U.S. Appl. No. 17/653,920 mailed Aug. 14, 2024.

(56) References Cited

OTHER PUBLICATIONS

Final Office Action for U.S. Appl. No. 17/808,354 mailed Apr. 10, 2024.
Final Office Action for U.S. Appl. No. 18/134,857 mailed Jul. 25, 2024.
Final Office Action for U.S. Appl. No. 18/140,163 mailed Mar. 27, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/904,868 mailed Mar. 12, 2024.
Non-Final Office Action for U.S. Appl. No. 17/378,015 mailed Jul. 5, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/749,340 mailed Aug. 14, 2024.
Non-Final Office Action for U.S. Appl. No. 18/003,029 mailed Mar. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 17/326,980 mailed Apr. 5, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/501,591 mailed Jul. 31, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/664,914 mailed Jul. 26, 2024.
Notice of Allowance for U.S. Appl. No. 18/140,163 mailed Aug. 21, 2024.
Notice of Allowance for U.S. Appl. No. 18/198,464 mailed Apr. 17, 2024.
Notice of Allowance for U.S. Appl. No. 18/198,464 mailed Jul. 30, 2024.
Restriction Requirement for U.S. Appl. No. 17/527,769 mailed Jun. 17, 2024.
Restriction Requirement for U.S. Appl. No. 17/625,941 mailed Aug. 7, 2024.
Restriction Requirement for U.S. Appl. No. 17/667,097 mailed Mar. 20, 2024.
U.S. Appl. No. 17/013,822, filed Sep. 7, 2020.
U.S. Appl. No. 17/444,792, filed Aug. 10, 2021.
U.S. Appl. No. 18/249,577, filed Oct. 19, 2021.
U.S. Appl. No. 18/610,523, filed Mar. 20, 2024.
U.S. Appl. No. 18/662,216, filed May 13, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 63/561,893, filed Dec. 11, 2023.
U.S. Appl. No. 63/568,615, filed Mar. 22, 2024.
U.S. Appl. No. 63/683,428, filed Aug. 15, 2024.

(56) References Cited

OTHER PUBLICATIONS

"OBLONG", Cambridge Dictionary, https://dictionary.cambridge.org/dictionary/english/oblong, 2024, 1 page.

Britannica, "Polyolefin", Britannica Online Encyclopedia, T. Editors of Encyclopaedia, https://www.britannica.com/science/polyolefin, Jul. 26, 2012.

Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.

Wikipedia Article, "Decibel", https://web.archive.org/web/2020041521917/https://en.wikipedia/org/wiki/Decibel last accessed Mar. 11, 2024, 21 pages.

Wikipedia Article, "Fiberglass", https://web.archive.org.web/20200309194847/https://en.wikipedia.org/wiki/Fiberglass last accessed Mar. 11, 2024.

\* cited by examiner

FLUID COLLECTION ASSEMBLIES INCLUDING AT LEAST ONE SECUREMENT BODY

CROSS-REFERENCE TO RELATED APPLICATIONS

This application claims priority to U.S. Provisional Patent Application No. 63/134,450 filed on Jan. 6, 2021, the disclosure of which is incorporated herein, in its entirety, by this reference.

BACKGROUND

A patient may have limited or impaired mobility such that typical urination processes are challenging or impossible. For example, the patient may have surgery or a disability that impairs mobility. In another example, the patient may have restricted travel conditions such as those experience by pilots, drivers, and workers in hazardous areas. Additionally, fluid collection from the patient may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection assemblies continue to seek new and improved devices, systems, and methods to collect urine.

SUMMARY

Embodiments disclosed herein include fluid collection assemblies with at least one securement body, fluid collection systems including the same, and methods of using the same. In an embodiment, a fluid collection assembly is disclosed. The fluid collection assembly includes a fluid impermeable barrier at least defining a chamber, at least one opening, and a fluid outlet. The fluid collection assembly also includes at least one porous material disposed in the chamber and at least one securement body configured to limit movement of the fluid collection assembly relative to a region about a urethral opening of a patient. The at least one securement body includes at least one of a plurality of fibers exhibiting an average lateral dimension of about 5 μm or less, a plurality of suction cups, or at least one friction material exhibiting a coefficient of static friction that is greater than at least a portion of the at least one porous material.

In an embodiment, a fluid collection system is disclosed. The fluid collection system includes a fluid storage container configured to hold one or more bodily fluids therein. The fluid collection system also includes a fluid collection assembly. The fluid collection assembly includes a fluid impermeable barrier at least defining a chamber, at least one opening, and a fluid outlet. The fluid collection assembly also includes at least one porous material disposed in the chamber and at least one securement body configured to limit movement of the fluid collection assembly relative to a region about a urethral opening of a patient. The at least one securement body includes at least one of a plurality of fibers exhibiting an average lateral dimension of about 5 μm or less, a plurality of suction cups, or at least one friction material exhibiting a coefficient of static friction that is greater than at least a portion of the at least one porous material. The fluid collection system further includes a vacuum source in fluid communication with the fluid storage container and the fluid collection assembly. The vacuum source is configured to draw the one or more bodily fluids from the fluid collection assembly and deposit the one or more bodily fluids in the fluid storage container via one or more conduits.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
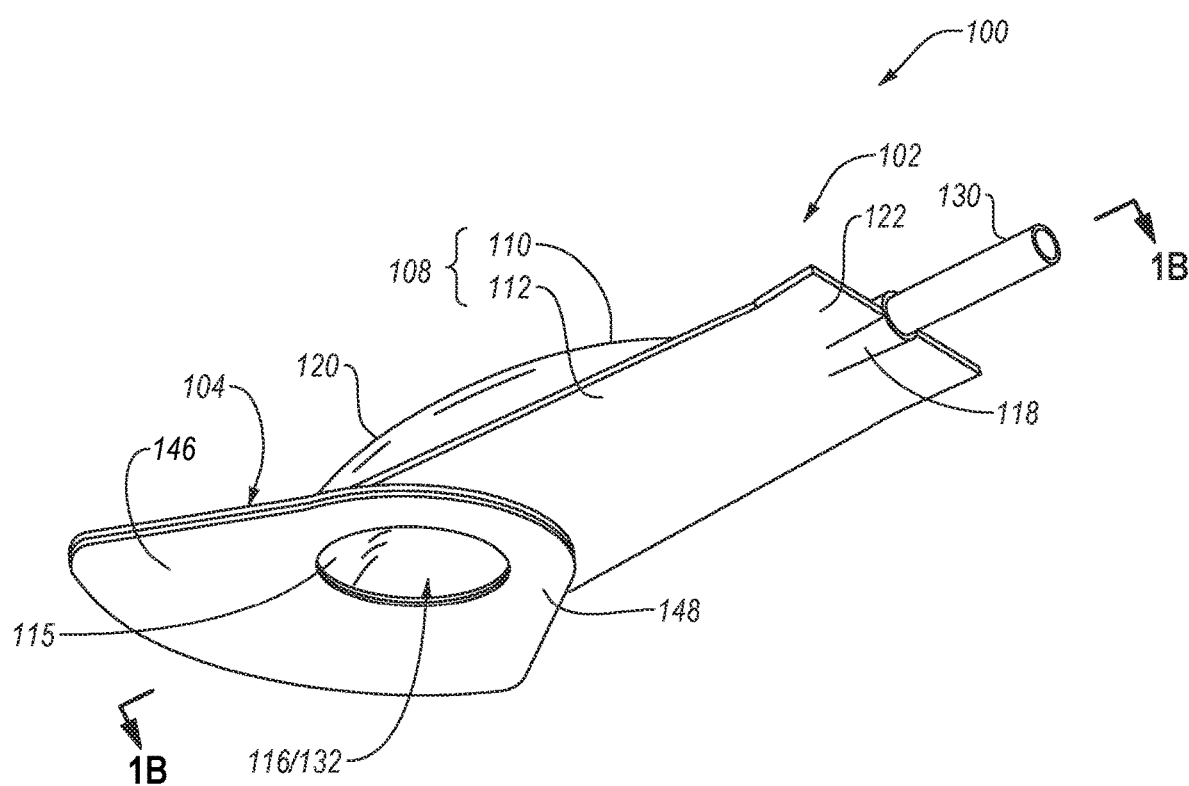
FIG. 1A is an isometric view of a fluid collection assembly, according to an embodiment.

Embodiments disclosed herein include fluid collection assemblies with at least one securement body, fluid collection systems including the same, and methods of using the same. An example fluid collection assembly may include a male fluid collection assembly configured to receive one or more bodily fluids (e.g., urine, blood, sweat, etc.) from a male urethral opening or a female fluid collection assembly configured to receive the bodily fluids from a female urethral opening. The fluid collection assembly includes a fluid impermeable barrier that at least defines a chamber, at least one opening, and a fluid outlet. The fluid collection assembly also includes at least one porous material disposed in the chamber and at least one securement body. The securement body is disposed on one or more components of the fluid collection assembly and is configured to limit movement of the fluid collection assembly relative to a region about a urethral opening of the patient. For example, the securement body may be disposed on one or more of at least a portion of the fluid impermeable barrier, at least a portion of the porous material that extends across the opening, or a base. Examples of securement bodies include a plurality of fibers extending from at least one exterior surface of the fluid collection assembly, a plurality of suction cups, or a friction material that exhibits a coefficient of friction that is greater than at least a portion of the porous material.

During use, the fluid collection assembly is positioned adjacent to or receives the urethral opening of the patient. The patient may discharge one or more bodily fluids and the fluid collection assembly may receive the bodily fluids. However, movement of the fluid collection assembly may prevent the fluid collection assembly from receiving all or substantially all of the bodily fluids that are discharged by the patient. For example, movement of the fluid collection assembly may cause bodily fluids to leak. The leaked bodily fluids may create patient discomfort by causing the skin of the patient to remain moist, creating unsanitary conditions, requiring cleaning of the patient, and causing embarrassment to the patient.

Some conventional fluid collection assemblies rely on chemical adhesives or contact between the thighs of the patient and the fluid impermeable barrier to maintain the position of the fluid collection assembly and prevent bodily fluid leaks. However, the chemical adhesives may be painful to remove from the patient since such chemical adhesives may be attached to hair and sensitive regions of the patient (e.g., the region about the urethral opening). Further, the contact between the thighs of the patient and the fluid impermeable barrier may be unable to maintain the position of the fluid collection assembly because the patient is too thin (e.g., has gaps between the thighs that prevent contact with the fluid impermeable barrier) or the patient moves. The fluid collection assemblies that include at least one securement body (e.g., the plurality of fibers, the friction material, and/or the plurality of suction cups) are improvements over such conventional fluid collection assemblies. In an example, the securement body may engage the patient to limit movement of the fluid collection assembly but, unlike chemical adhesives, the securement body may be easily removed when certain forces are applied thereto. Further, the securement body may maintain the position of the fluid collection assembly even when the patient is too thin for the thighs of the patient to contact the fluid collection assembly and/or when the patient moves.

Figure 1B:
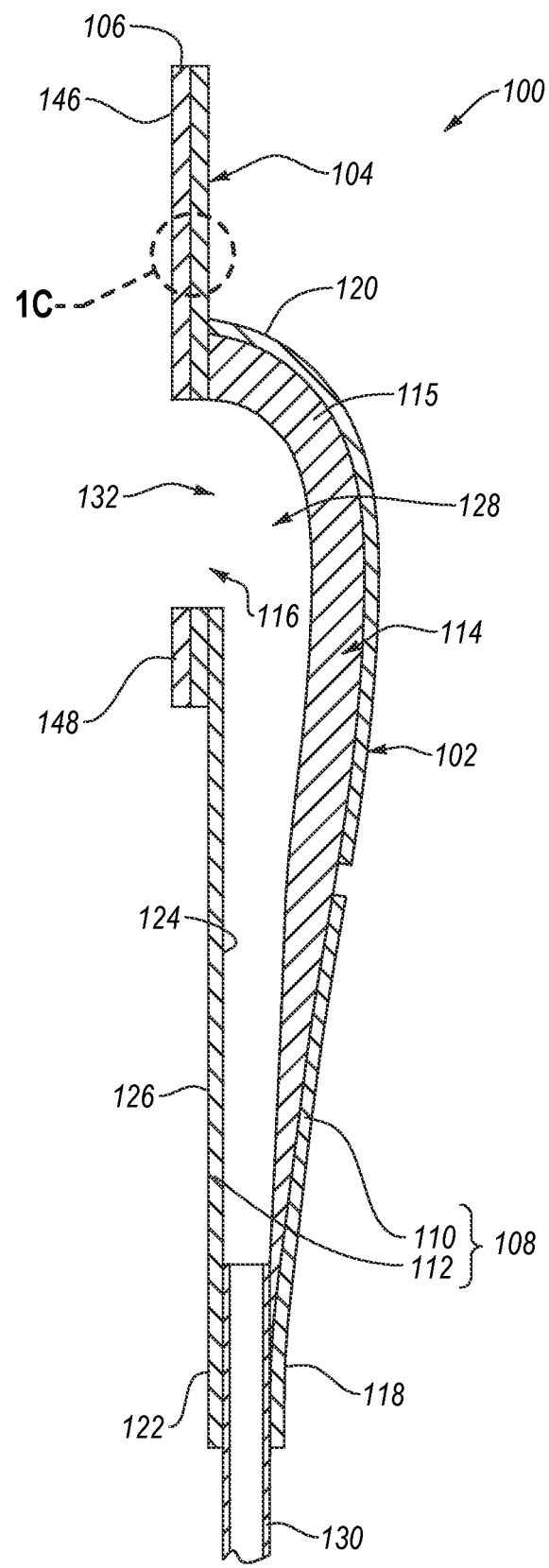
FIG. 1B is a cross-sectional view of the fluid collection assembly taken along plane 1B-1B shown in FIG. 1A, according to an embodiment.

FIG. 1A is an isometric view of a fluid collection assembly 100, according to an embodiment. FIG. 1B is a cross-sectional view of the fluid collection assembly 100 taken along plane 1B-1B shown in FIG. 1A, according to an embodiment. The fluid collection assembly 100 is an example of a male fluid collection assembly though, in some embodiments, the fluid collection assembly 100 may be used to receive bodily fluids from a female urethral opening. The fluid collection assembly 100 includes a sheath 102 and a base 104. The base 104 is configured to be attached (e.g., permanently attached or configured to be permanently attached) to the sheath 102. The base 104 is also configured to be attached to the region about the urethral opening (e.g., penis) of the patient. The base 104 includes at least one securement body 106.

The sheath 102 includes a fluid impermeable barrier 108 that is at least partially formed from a first panel 110 and a second panel 112. The first panel 110 and the second panel 112 may be attached or integrally formed together (e.g., exhibits single piece construction). In an embodiment, as illustrated, the first panel 110 and the second panel 112 are distinct sheets. The fluid impermeable barrier 108 also defines a chamber 114 between the first panel 110 and the second panel 112, an opening 116 at a first end region 120 of the sheath 102, and an fluid outlet 118 at a second end region 122 of the sheath 102. The sheath 102 also includes at least one porous material 115 disposed in the chamber 114.

The inner surface(s) 124 of the fluid impermeable barrier 108 (e.g., inner surfaces of the first and second panels 110, 112) at least partially defines the chamber 114 within the fluid collection assembly 100. The fluid impermeable barrier 108 temporarily stores the bodily fluids in the chamber 114. The fluid impermeable barrier 108 may be formed of any suitable fluid impermeable material(s), such as a fluid impermeable polymer (e.g., silicone, polypropylene, polyethylene, polyethylene terephthalate, neoprene, a polycarbonate, etc.), a metal film, natural rubber, another suitable material, or combinations thereof. As such, the fluid impermeable barrier 108 substantially prevents the bodily fluids from passing through the fluid impermeable barrier 108. In an example, the fluid impermeable barrier 108 may be air permeable and fluid impermeable. In such an example, the fluid impermeable barrier 108 may be formed of a hydrophobic material that defines a plurality of pores. At least one or more portions of at least an outer surface 126 of the fluid impermeable barrier 108 may be formed from a soft and/or smooth material, thereby reducing chaffing.

In an embodiment, at least one of the first panel 110 or the second panel 112 is formed from an at least partially transparent fluid impermeable material, such as polyethylene, polypropylene, polycarbonate, or polyvinyl chloride. Forming at least one of the first panel 110 or the second panel 112 from an at least partially transparent fluid impermeable material allows a person (e.g., medical practitioner) to examiner the penis. In some embodiments, both the first panel 110 and the second panel 112 are formed from at least partially transparent fluid impermeable material. Selecting at least one of the first panel 110 or the second panel 112 to be formed from an at least partially transparent impermeable material allows the penis to be examined without detaching the entire fluid collection assembly 100 from the region about the penis. For example, the chamber 114 may include a penis receiving area 128 that is configured to receive the penis of the individual when the penis extends into the chamber 114. The penis receiving area 128 may be defined by at least the porous material 115 and at least a portion of the at least partially transparent material of the first panel 110 and/or the second panel 112. In other words, the porous material 115 is positioned in the chamber 114 such that the porous material 115 is not positioned between the penis and at least a portion of the transparent portion of the first panel 110 and/or second panel 112 when the penis is inserted into the chamber 114 through the opening 116. The porous material 115 is generally not transparent and, thus, the portion of the at least partially transparent material of the first panel 110 and/or the second panel 112 that defines the penis receiving area 128 forms a window which allows the person to view into the penis receiving area 128 and examine the penis.

The opening 116 defined by the fluid impermeable barrier 108 provides an ingress route for fluids to enter the chamber 114 when the penis is a buried penis and allow the penis to enter the chamber 114 (e.g., the penis receiving area 128) when the penis is not buried. The opening 116 may be defined by the fluid impermeable barrier 108 (e.g., an inner edge of the fluid impermeable barrier 108). For example, the opening 116 is formed in and extends through the fluid impermeable barrier 108 thereby enabling bodily fluids to enter the chamber 114 from outside of the fluid collection assembly 100.

The fluid impermeable barrier 108 defines an fluid outlet 118 sized to receive an conduit 130. The conduit 130 may be at least partially disposed in the chamber 114 or otherwise in fluid communication with the chamber 114 through the fluid outlet 118. The fluid outlet 118 may be sized and shaped to form an at least substantially fluid tight seal against the conduit 130 thereby substantially preventing the bodily fluids from escaping the chamber 114. In an embodiment, the fluid outlet 118 may be formed from a portion of the first panel 110 and the second panel 112 that are not attached or integrally formed together. In such an embodiment, the fluid impermeable barrier 108 may not include a cap exhibiting a rigidity that is greater than the portions of the fluid impermeable barrier 108 thereabout which may facilitate manufacturing of the fluid collection assembly 100 may decreasing the number of parts that are used to form the fluid collection assembly 100 and may decrease the time required to manufacture the fluid collection assembly 100. The lack of the cap may make securing the conduit 130 to the fluid outlet 118 using interference fit to be difficult though, it is noted, attaching the conduit 130 to the fluid outlet 118 may still be possible. As such, the conduit 130 may be attached to the fluid outlet 118 (e.g., to the first and second panels 110, 112) using an adhesive, a weld, or otherwise bonding the fluid outlet 118 to the fluid outlet 118. Attaching the conduit 130 to the fluid outlet 118 may prevent leaks and may prevent the conduit 130 from inadvertently becoming detached from the fluid outlet 118. In an example, the conduit 130 may be attached to the fluid outlet 118 in the same manufacturing step that attaches the first and second panels 110, 112 together.

As previously discussed, the sheath 102 includes at least one porous material 115 disclosed in the chamber 114. The porous material 115 may direct the bodily fluids to one or more selected regions of the chamber 114, such as away from the penis and towards the fluid outlet 118. In an embodiment, the porous material 115 includes a fluid permeable membrane extending across the opening 116 and a fluid permeable support since the fluid permeable membrane may be formed from a relatively foldable, flimsy, or otherwise easily deformable material. For example, the fluid permeable support may be positioned such that the fluid permeable membrane is disposed between the fluid permeable support and the fluid impermeable barrier 108. As such, the fluid permeable support may support and maintain the position of the fluid permeable membrane. The fluid permeable membrane may include fabric, such as a gauze (e.g., a silk, linen, or cotton gauze), another soft fabric, or another smooth fabric. The fluid permeable support may include any of the fluid permeable membrane materials disclosed above in a more dense or rigid form, a porous polymer (e.g., nylon, polyester, polyurethane, polyethylene, polypropylene, etc.) structure or an open cell foam, spun nylon fiber, a natural material (e.g., cotton, wool, silk, or combinations thereof), any other suitable material, or combinations thereof. In an embodiment, the porous material 115 may only include one of the fluid permeable membrane or the fluid permeable support. In an embodiment, the porous material 115 includes a first porous layer, a second porous layer, and a plurality of fibers forming a layer between the first and second layers.

In an embodiment, the porous material 115 may be configured to wick any bodily fluids away from the opening 116, thereby preventing the bodily fluids from escaping the chamber 114. The permeable properties referred to herein may be wicking, capillary action, diffusion, or other similar properties or processes, and are referred to herein as "permeable" and/or "wicking." Such "wicking" may not include absorption of the bodily fluids into the wicking material. Put another way, substantially no absorption of the bodily fluids into the material may take place after the material is exposed to the bodily fluids and removed from the bodily fluids for a time. While no absorption is desired, the term "substantially no absorption" may allow for nominal amounts of absorption of the bodily fluids into the wicking material (e.g., absorbency), such as less than about 30 wt % of the dry weight of the porous material, less than 20 wt %, less than 15 wt %, less than 10 wt %, less than about 7 wt %, less than about 5 wt %, less than about 3 wt %, less than about 2 wt %, less than about 1 wt %, or less than about 0.5 wt % of the dry weight of the porous material. The wicking material may also wick the bodily fluids generally towards an interior of the chamber 114, as discussed in more detail below. In an embodiment, the porous material 115 may include at least one absorbent or adsorbent material.

In an embodiment, the porous material 115 may be a sheet. Forming the porous material 115 as a sheet may facilitate the manufacturing of the fluid collection assembly 100. For example, forming the porous material 115 as a sheet allows the first panel 110, the second panel 112, and the porous material 115 to each be sheets. During the manufacturing of the fluid collection assembly 100, the first panel 110, the second panel 112, and the porous material 115 may be stacked and then attached to each other in the same manufacturing step. For instance, the porous material 115 may exhibit a shape that is the same size or, more preferably, slightly smaller than the size of the first panel 110 and the second panel 112. As such, attaching the first panel 110 and the second panel 112 together along the outer edges thereof may also attach the porous material 115 to the first panel 110 and the second panel 112. The porous material 115 may be slightly smaller than the first panel 110 and the second panel 112 such that the first panel 110 and/or the second panel 112 extend around the porous material 115 such that the porous material 115 does not form a passageway through the fluid impermeable barrier 108 through which the bodily fluids may leak. Also, attaching the porous material 115 to the first panel 110 and/or the second panel 112 may prevent the porous material 115 from significantly moving in the chamber 114, such as preventing the porous material 115 from bunching together near the fluid outlet 118. In an example, the porous material 115 may be attached to the first panel 110 or the second panel 112 (e.g., via an adhesive) before or after attaching the first panel 110 to the second panel 112. In an example, the porous material 115 may merely be disposed in the chamber 114 without attaching the porous material 115 to at least one of the first panel 110 or the second panel 112. In an embodiment, as will be discussed in more detail below, the porous material 115 may exhibit shapes other than a sheet, such as a hollow generally cylindrical shape.

Generally, the sheath 102 is substantially flat when the penis is not in the penis receiving area 128 and the sheath 102 is resting on a flat surface. The sheath 102 is substantially flat because the fluid impermeable barrier 108 is formed from the first panel 110 and the second panel 112 instead of a generally tubular fluid impermeable barrier. Further, as previously discussed, the porous material 115 may be a sheet, which also causes the sheath 102 to be substantially flat. The sheath 102 may also be substantially flat because the fluid collection assembly 100 may not include relatively rigid rings or caps that exhibit a rigidity that is greater than the portions of the fluid impermeable barrier 108 thereabout since such rings and caps may inhibit the sheath 102 being substantially flat. It is noted that the sheath 102 is described as being substantially flat because at least one of the porous material 115 may cause a slight bulge to form in the sheath 102 depending on the thickness of the porous material 115, the fluid outlet 118 and/or conduit 130 may cause a bulge thereabout, or the base 104 may pull on portions of the sheath 102 thereabout. It is also noted that the sheath 102 may also be compliant and, as such, the sheath 102 may not be substantially flat during use since, during use, the sheath 102 may rest on a non-flat surface (e.g., may rest on the testicles, the perineum, and/or between the thighs) and the sheath 102 may conform to the surface of these shapes.

The ability of the sheath 102 to be substantially flat when the penis is not in the penis receiving area 128 and the sheath 102 is resting on a flat surface allows the fluid collection assembly 100 to be used with a buried and a non-buried penis. For example, when the fluid collection assembly 100 is being used with a buried penis, the penis does not extend into the penis receiving area 128 which causes the sheath 102 to lie relatively flat across the aperture 132 of the base 104. When the sheath 102 lies relatively flat across the aperture 132, the porous material 115 extends across the opening 116 and the aperature 132 and is in close proximity to the buried penis. As such, the porous material 115 prevents or inhibits pooling of bodily fluids discharged from the buried penis against the skin of the individual since the porous material 115 will receive and remove at least a significant portion of the bodily fluids that would otherwise pool against the skin of the individual. Thus, the skin of the individual remains dry thereby improving comfort of using the fluid collection assembly 100 and preventing skin degradation. However, unlike other conventional fluid collection assemblies that are configured to be used with buried penises, the fluid collection assembly 100 may still be used with a non-buried penis since the non-buried penis can still be received into the penis receiving area 128, even when the penis is fully erect. Additionally, the ability of the sheath 102 to be substantially flat allows the fluid collection assembly 100 to be used more discretely than if the sheath 102 was not substantially flat thereby avoiding possibly embarrassing scenarios.

When the sheath 102 is substantially flat, the porous material 115 occupies substantially all of the chamber 114 and the penis receiving area 128 is collapsed (shown as being non-collapsed in FIG. 1B for illustrative purposes to show the penis receiving area 128). In other words, the sheath 102 may not define an region that is constantly unoccupied by the porous material 115. When the porous material 115 occupies substantially all of the chamber 114, the bodily fluids discharged into the chamber 114 are unlikely to pool for significant periods of time since pooling of the bodily fluids may cause sanitation issues, cause an odor, and/or may cause the skin of the individual to remain in contact with the bodily fluids which may cause discomfort and skin degradation.

As previously discussed, the first panel 110, the second panel 112, and the porous material 115 may be selected to be relatively flexible. The first panel 110, the second panel 112, and the porous material 115 are relatively flexible when the first panel 110, the second panel 112, and the porous material 115, respectively, are unable to maintain their shape when unsupported. The flexibility of the first panel 110, the second panel 112, and the porous material 115 may allow the sheath 102 to be substantially flat, as discussed above. The flexibility of the first panel 110, the second panel 112, and the porous material 115 may also allow the sheath 102 to conform to the shape of the penis even when the size and shape of the penis changes (e.g., becomes erect) and to minimize any unoccupied spaces in the chamber 114 in which bodily fluids may pool.

As previously discussed, the fluid collection assembly 100 includes a base 104 that is configured to be attached to the sheath 102. For example, the base 104 is configured to be permanently attached to the sheath 102. The base 104 is configured to be permanently attached to the sheath 102 when, for example, when the fluid collection assembly 100 is provided with the base 104 permanently attached to the sheath 102 or the base 104 is provided without being permanently attached to the sheath 102 but is configured to be permanently attached to the sheath 102 at some point in the future. Permanently attached means that the sheath 102 cannot be detached from the base 104 without damaging at least one of the sheath 102 or the base 104, using a blade to separate the sheath 102 from the base 104, and/or using chemicals to dissolve the adhesive that attaches the sheath 102 from the base 104. The base 104 may be permanently attached to the sheath 102 using an adhesive, sewing, heat sealing, RF welding, or US welding. In an embodiment, the base 104 is configured to be reversibly attached to the sheath 102.

As previously discussed, the base 104 includes an aperture 132. The base 104 is permanently attached to the first end region 120 of the sheath 102 such that the aperture 132 is aligned with the opening 116.

The base 104 is sized, shaped, and made of a material to be coupled to the skin that surrounds the penis (e.g., mons pubis, thighs, testicles, and/or perineum) and have the penis disposed therethrough. For example, the base 104 may define an aperture 132 configured to have the penis positioned therethrough. In an example, the base 104 may exhibit the general shape or contours of the skin surface that the base 104 is configured to be coupled with. The base 104 may be flexible, thereby allowing the base 104 to conform to any shape of the skin surface and mitigate the base 104 pulling the on skin surface. The base 104 may extend laterally past the sheath 102 thereby increasing the surface area of the skin of the individual to which the fluid collection assembly 100 may be attached compared to a substantially similar fluid collection assembly 100 that did not include a base.

Figure 1C:
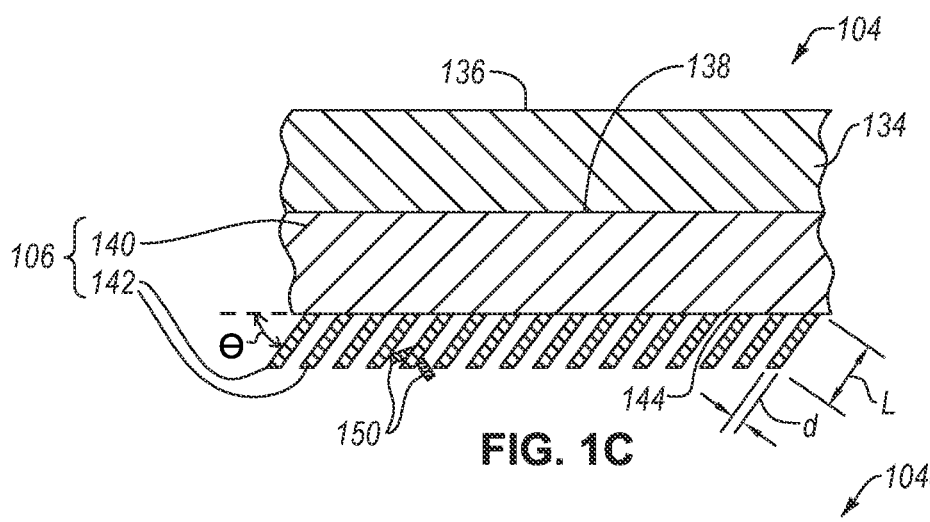
FIG. 1C is an enlarged cross-sectional schematic of a portion of the base, according to an embodiment.

FIG. 1C is an enlarged cross-sectional schematic of a portion of the base 104, according to an embodiment. As illustrated, the base 104 may include a substrate 134. The substrate 134 includes a top surface 136 and a bottom surface 138. The top surface 136 is closer to the sheath 102 than the bottom surface 138 while the bottom surface 138 is, during use, closer to the skin of the individual than the top surface 136. In an embodiment, a portion of the top surface 136 may be attached to or configured to be attached to the sheath 102.

The substrate 134 may be formed from any suitable material. In an embodiment, the substrate 134 may be formed from fluid impermeable material(s), such as any of the fluid impermeable materials disclosed herein. In such an embodiment, the substrate 134 inhibits bodily fluids from leaking therethrough. In an embodiment, the substrate 134 is formed from a porous material, such as a porous material that is air-permeable and water impermeable (e.g., a hydrophobic porous material). In such an embodiment, the substrate 134 may allow air to flow therethrough thereby encouraging fluid flow through the fluid collection assembly 100 and preventing a suction force provided to the fluid collection assembly 100 from giving the patient a hickie. In an embodiment, the substrate 134 may be formed from a flexible material and/or may exhibit a relatively thin thickness (e.g., less than about 2 mm, less than about 1 mm, less than about 0.5 mm, or in ranges of about 0.25 mm to about 0.75 mm, about 0.5 mm to about 1 mm, about 0.75 mm to about 1.5 mm, or about 1 mm to about 2 mm). The flexibility and/or thickness of the substrate 134 may allow the substrate 134 to be shaped to conform to the shape of the region about the urethral opening (e.g., mons pubis, testicles, etc.) without pulling on the region about the urethral opening.

The base 104 also include a securement body 106. The securement body 106 includes a support 140 that is distinct from the substrate 134. At least a portion of the support 140 is attached to at least a portion of bottom surface 138 of the substrate 134. The support 140 may be attached to the substrate 134 using any suitable technique, such as with an adhesive, ultrasonic welding, etc. Generally, the attachment between the substrate 134 and the support 140 is greater than a maximum attachment between the securement body 106 and the skin of the patient such that detaching the base 104 from the patient is unlikely to detach the support 140 from the substrate 134. It is noted that the securement body 106 and the support 140 may be attached to components of the fluid collection assembly 100 other than or in addition to the base 104, as will be discussed in more detail below.

The support 140 may be formed from any suitable material. In an embodiment, the support 140 may be formed from fluid impermeable material(s), such as any of the fluid impermeable materials disclosed herein. In such an embodiment, the support 140 inhibits bodily fluids from leaking therethrough. In an embodiment, the support 140 is formed from a porous material, such as a porous material that is air-permeable and water impermeable (e.g., a hydrophobic porous material). In such an embodiment, the support 140 may allow air to flow therethrough thereby encouraging fluid flow through the fluid collection assembly 100 and preventing a suction force provided to the fluid collection assembly 100 from giving the patient a hickie. In an embodiment, the support 140 may be formed from a flexible material and/or may exhibit a relatively thin thickness (e.g., less than about 2 mm, less than about 1 mm, less than about 0.5 mm, or in ranges of about 0.25 mm to about 0.75 mm, about 0.5 mm to about 1 mm, about 0.75 mm to about 1.5 mm, or about 1 mm to about 2 mm). The flexibility and/or thickness of the support 140 may allow the support 140 to be shaped to conform to the shape of the region about the urethral opening (e.g., mons pubis, testicles, etc.) without pulling on the region about the urethral opening.

The securement body 106 includes a plurality of fibers 142 extending from support 140. The plurality of fibers 142 are configured to attach the base 104 to the region about the urethral opening. The plurality of fibers 142 exhibit a large surface area due to the relatively small lateral dimensions d (e.g., diameters) thereof, as discussed in more detail below. The large surface area of the fibers 142 cause the fibers 142 to exhibit sufficiently large Van der Waal forces with the region about the urethral opening (e.g., the skin and hair about the urethral opening) that the fibers 142 securely attach the base 104 to the region about the urethral opening. In some embodiments, the fibers 142 may attach the base 104 to the region about the urethral opening as strongly as some chemical adhesives (e.g., hydrogels) when certain forces are applied to the base 104. However, the fibers 142 remain part of the base 104 when the base 104 is detached from the region about the urethral opening unlike chemical adhesives which may leave a film attached to the region about the urethral opening. In an example, since the fibers 142 remain part of the base 104, at least the base 104 may be reused. In such an example, the base 104 may be detached from the region about the urethral opening to allow for examination of the urethral opening and the region about the urethral opening (e.g., regardless if the panels are transparent) and, after examination, the base 104 may be reattached to the region about the urethral opening. Additionally or alternatively, after detaching the base 104 from the region about the urethral opening, the base 104 and, optionally, the sheath 104 may be washed and reused with the same or a new patient. In an example, the fibers 142 may be able to attach the base 104 to the region about the urethral opening when the region about the urethral opening is wet, dry, shaved, or hairy.

The fibers 142 may be selected to exhibit an average lateral dimension d. As used herein, the average lateral dimension d may refer to the average lateral dimension of one fiber 142 at a single location, the average lateral dimension of one fiber 142 averaged along a length thereof, or the average lateral dimension averaged across at least some (e.g., all) of the fibers 142. The average lateral dimension d may be selected to be less than about 10 μm, less than about 8 μm, less than about 6 μm, less than about 5 μm, less than about 4 μm, less than about 3 μm, less than about 2.5 μm, less than about 2 μm, less than about 1.5 μm, less than about 1 μm, less than about 750 nm, less than about 600 nm, less than about 500 nm, less than about 400 nm, less than about 300 nm, less than about 250 nm, less than about 200 nm, less than about 150 nm, less than about 100 nm, less than about 75 nm, less than about 50 nm, less than about 25 nm, less than about 10 nm, or in ranges of about 5 nm to about 25 nm, about 10 nm to about 50 nm, about 25 nm to about 75 nm, about 50 nm to about 100 nm, about 75 nm to about 150 nm, about 100 nm to about 200 nm, about 150 nm to about 300 nm, about 200 nm to about 400 nm, about 300 nm to about 500 nm, about 400 nm to about 600 nm, about 500 nm to about 750 nm, about 600 nm to about 1 μm, about 750 μm to about 1.5 μm, about 1 μm to about 2 μm, about 1.5 μm to about 3 μm, about 2 μm to about 4 μm, about 3 μm to about 5 μm, about 4 μm to about 7.5 μm, or about 5 μm to about 10 μm. The average lateral dimension d may be selected based on a number of factors.

In an example, the average lateral dimension d may be selected based on the desired adhesion between the securement body 106 and the region about the urethral opening. For instance, decreasing the average lateral dimension d increases the surface area of the fibers 142. The Vander der Waal forces between the fibers 142 and the region about the urethral opening increases as the surface area of the fibers 142 increase and the adhesion between the securement body 106 and the region about the urethral opening increases as the Vander de Waal forces increase. It is noted that the adhesion between the securement body 106 and the region about the urethral opening also depends on other factors, such as the number of fibers per unit of surface area of the support 140 and the length of the fibers 142.

In an example, the average lateral dimension d of the fibers 142 may be selected based on the material that forms the fibers 142. For instance, as previously discussed, the Vander der Waal forces between the fibers 142 and the region about the urethral opening depends on the surface area of the fibers 142 that are proximate to the region about the urethral opening. The surface area of the fibers 142 that are proximate to the region about the urethral opening may depend on the flexibility of the fibers 142. The flexibility of the fibers 142 depends inversely to the average lateral dimension d of the fibers 142 and inversely to the Young's modulus (i.e., modulus of elasticity) of the material that forms the fibers 142. As such, the average lateral dimension d may need to be increased as the Young's modulus of the material that forms the fibers 142 is decreased, and vice versa. In an embodiment, the fibers 142 are formed from a polymer, such as polyimide, polypropylene, polydimethylsiloxane, or any other suitable polymer. In such an embodiment, the average lateral dimension d of the fibers 142 may depend on the molecular weight of the polymer. In an embodiment, the fibers 142 are formed from carbon nanotubes. In such an embodiment, the fibers 142 may exhibit an average lateral dimension d that less than 100 nm, less than 50 nm, or more particularly less than 25 nm.

In an example, the average lateral dimension d of the fibers 142 may depend on the average length l of the fibers 142. For instance, increasing the average length l may increase the likelihood that the fibers 142 become tangled. Tangling the fibers 142 may prevent some of the fibers 142 from pressing against the region of the urethral opening that would press against the region about the urethral opening if not for the tangling. Thus, even though increasing the average length l generally increases the surface area of the fibers 142, increasing the average length l above a threshold value may cause the fibers 142 to become tangled and decrease the adhesion between the securement body 106 and the region about the urethral opening. The threshold value may be increased by increasing the average lateral dimension d of the fibers 142. Thus, increasing the average lateral dimension d allows the lengths of the fibers 142 to be increased without the accompanying issues of entanglement. It is noted that, as used herein, the average length l may refer to the length of a single fiber 142, the length averaged across some of the fibers 142, or the length averaged across all of the fibers 142.

In an embodiment, the average length l of the fibers 142 may be selected to be greater than about 500 nm, greater than about 750 nm, greater than about 1 µm, greater than about 2 µm, greater than about 3 µm, greater than about 5 µm, greater than about 7.5 µm, greater than about 10 µm, greater than about 15 µm, greater than about 25 µm, greater than about 50 µm, greater than about 75 µm, greater than about 100 µm, or in ranges of about 500 nm to about 1 µm, about 750 nm to about 1.5 µm, about 1 µm to about 2 µm, about 1.5 µm to about 3 µm, about 2 µm to about 5 µm, about 3 µm to about 7.5 µm, about 5 µm to about 10 µm, about 7.5 µm to about 15 µm, about 10 µm to about 25 µm, about 15 µm to about 50 µm, about 25 µm to about 75 µm, or about 50 µm to about 100 µm. As previously discussed, the average length l of the fibers 142 may be selected based on the average lateral dimension d and desired surface area of the fibers 142 that is proximate to the region about the urethral opening. The average length l of the fibers 142 may also be selected based on the material(s) that form the fibers 142 since increasing and decreasing the Young's modulus of the material(s) that form the fibers 142 increases and decreases, respectively, the entanglement threshold.

Generally, the average length l of the fibers 142 are greater than the average lateral dimension d. For example, the average length l of the fibers 142 may be selected to be greater than the average lateral dimension d by a factor that is at least about 5, at least about 10, at least about 20, at least about 30, at least about 50, at least about 75, at least about 100, at least about 150, at least about 200, at least about 300, at least about 500, or in ranges of about 5 to 20, about 20 to about 30, about 20 to about 30, about 30 to about 75, about 50 to about 100, about 75 to about 150, about 100 to about 200, about 150 to about 300, or about 200 to about 500.

The fibers 142 may extend from the support 140 at an average angle $\theta$. The average angle $\theta$ is an oblique angle. The angle $\theta$ is the average smallest angle that may be measured from an outer surface 144 of the support 140 to a portion of the fibers 142 adjacent to the support 140 when no external force is pressing against the fibers 142. The average angle $\theta$ may be the angle $\theta$ measure between one, some, or all of the fibers 142. The angle $\theta$ may be about 1° to about 10°, about 5° to about 15°, about 10° to about 20°, about 15° to about 25°, about 20° to about 30°, about 25° to about 35°, about 30° to about 40°, about 35° to about 45°, about 40° to about 50°, about 45° to about 60°, about 55° to about 75°, or about 70° to about 89°. The average angle $\theta$ generally corresponds to the angle between the fibers 142 and the region about the urethral opening assuming the base 104 is sufficiently flexible that the base 104 generally corresponds to the region about the urethral opening. Decreasing the angle $\theta$ increases the surface area of the fibers 142 that are proximate to the region about the urethral opening which, in turn, increases the adhesion between the securement body 106 and the region about the urethral opening. Generally, decreasing the average angle $\theta$ to be less than about 45° and less than about 30° may allow the fibers 142 to be significantly better at resisting shear forces than if the average angle $\theta$ was greater than these values.

The average angle $\theta$ may be selected to facilitate attachment, detachment, and securement of the base 104 to the region about the urethral opening. In an example, referring to FIG. 1A, and the base 104 may include a first region 146 and a second region 148. The first region 146 is configured to be attached to the mons pubis while the second region 148 is configured to be attached around the shaft of the penis. The mons pubis exhibits a significantly larger surface area than the area around the shaft of the penis to which the base 104 may be attached. As such, the first region 146 may exhibit a larger surface area than the second region 148. In an embodiment, referring to FIG. 1C, the average angle $\theta$ is selected to be less than about 45° (e.g., less than about 30°) and such that at least most of the fibers 142 extend from the support 140 in a direction that generally extends from the second region 148 to the first region 146. In such an embodiment, during use, the base 104 may press into the region about the urethral opening when the patient is lying on the patient's backs such that significant adhesion is not necessary to maintain the base 104 attached to the region about the urethral opening. However, when the patient stands, the average angle $\theta$ may resist the shear forces caused by pulling the fluid collection assembly 100 downwards (e.g., towards the feet of the patient). In fact, pulling the fluid collection assembly 100 downwards may decrease the average angle $\theta$ thereby increasing adhesion of the base 104 to the region about the urethral opening. However, pulling the fluid collection assembly 100 upwards (e.g., towards the head) or perpendicular to the region about the urethral opening may decrease the average angle θ thereby decreasing adhesion between the securement body 106 and the region about the urethral opening. In other words, the securement body 106 may be more easily detached from the patient (e.g., detached less painfully) when the fluid collection assembly 100 is pulled upward or perpendicular from the region about the urethral opening.

It is noted that the average angle θ does not need to be selected such that the fibers 142 do not extend from the second region 148 to the first region 146. In an example, the average angle θ may be selected such that the fibers 142 extend from the first region 146 to the second region 148. In such an example, a large force pulling downward on the fluid collection assembly 100 may cause the securement body 106 to become detached from the patient which may be beneficial when the downward force is sufficient to cause patient pain if the securement body 106 did not become detached. In an example, the average angle θ may be selected such that the fibers 142 do not extend from the first region 146 to the second region 148 or from the second region 148 to the first region 146 (e.g., the fibers 142 extend in a sideways direction). In such an example, the securement body 106 may be used with a patient that remains mostly in-bed since the downward force applied to the fluid collection assembly 100 caused by standing is not likely to be a factor.

Figure 1D:
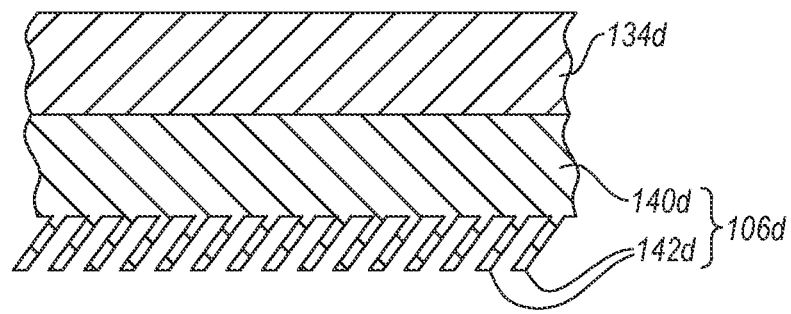
FIGS. 1D to 1F are cross-sectional schematics of different bases that may be used with the fluid collection assembly, according to different embodiments.
Figure 1E:
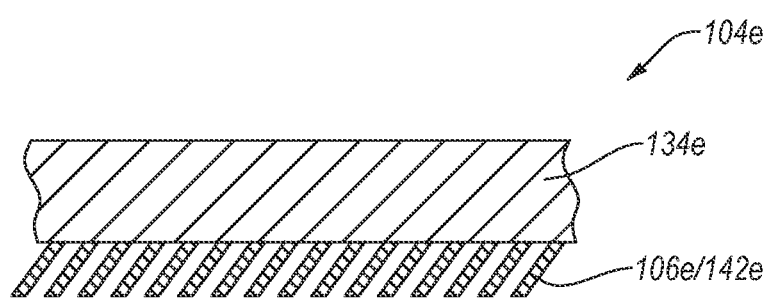
Figure 1F:
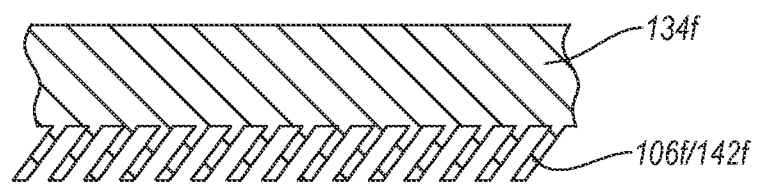

As discussed above, the average angle θ is relative to the outer surface 144 of the support 140. However, as will be discussed in more detail below, the fibers 142 may extend from at least one exterior surface of the fluid collection assembly 100 other than or in addition to the outer surface 144 of the support 140. For example, the fibers 142 may extend from the bottom surface 138 of the substrate 134 (as shown in FIGS. 1E and 1F) or the fluid impermeable barrier 108 (as discussed with regards to FIGS. 3A and 3B). As such, it is noted that the average angle θ is measure relative to the at least one exterior surface of the fluid collection assembly from which the fibers extend.

The securement body 106 may include at least 5,000 fibers per square centimeter of surface area of the outer surface 144 of the support 140 ("f/sc"), at least 10,000 f/sc, at least about 25,000 f/sc, at least about 50,000 f/sc, at least about 75,000 f/sc, at least about 100,000 f/sc, at least about 150,000 f/sc, at least about 200,000 f/sc, at least about 300,000 f/sc, at least about 500,000 f/sc, at least about 750,000 f/sc, at least about 1,000,000 f/sc, at least about 1,500,000 f/sc, at least about 2,500,000 f/sc, at least about 5,000,000 f/sc, at least about 10,000,000 f/sc, at least about 20,000,000 f/sc, or in ranges of about 10,000 f/sc to about 50,000 f/sc, about 25,000 f/sc to about 75,000 f/sc, about 50,000 f/sc to about 100,000 f/sc, about 75,000 f/sc to about 150,000 f/sc, about 100,000 f/sc to about 200,000 f/sc, about 150,000 f/sc to about 300,000 f/sc, about 200,000 f/sc to about 500,000 f/sc, about 300,000 f/sc to about 750,000 f/sc, about 500,000 f/sc to about 1,000,000 f/sc, about 750,000 f/sc to about 1,500,000 f/sc, about 1,000,000 f/sc to about 2,500,000 f/sc, about 1,500,000 f/sc to about 5,000,000 f/sc, about 2,500,000 f/sc to about 10,000,000 f/sc, or about 5,000,000 f/sc to about 20,000,000 f/sc. Increasing and decreasing number of fibers 142 per square centimeter of surface area of the outer surface 144 of the support 140 increases and decreases, respectively, the adhesion between the securement body 106 and the region about the urethral opening. As such, the number of fibers 142 per square centimeter of surface area of the outer surface 144 may be selected based on the desired adhesion, other factors that affect adhesion (e.g., average lateral dimension d, average length 1, etc.), and the maximum number of fibers 142 that may reasonably fit within the square centimeter.

In an embodiment, securement body 106 may include one or more branches 150 extending therefrom. The branches 150 may extend from or attached to a portion of the fibers 142 at or near the terminal end thereof. For illustrative purposes (i.e., to more clearly illustrated the fibers 142 and prevent clutter), only one of the fibers 142 are illustrated as having branches 150 extending therefrom. The branches 150 may increase the surface area of the fibers 142 which, in turn, increases the adhesion between the securement body 106 and the region about the urethral opening. The branches 150 exhibit an average diameter and an average length that is significantly less than the average lateral dimension d and the average length 1 of the fibers 142. For example, the average diameter and/or average length of the branches 150 may be less than the average lateral dimension d and/or average length 1 of the fibers 142, respectively, by at least about 2, at least about 5, at least about 10, at least about 15, at least about 20, at least about 30, at least about 40, at least about 50, or in ranges of about 2 to about 10, about 5 to about 15, about 10 to about 20, about 15 to about 30, about 20 to about 40, or about 30 to about 50. In an example, the average diameter of the branches 150 may exhibit be less than about less than about 2 μm, less than about 1.5 μm, less than about 1 μm, less than about 750 nm, less than about 600 nm, less than about 500 nm, less than about 400 nm, less than about 300 nm, less than about 250 nm, less than about 200 nm, less than about 150 nm, less than about 100 nm, less than about 75 nm, less than about 50 nm, less than about 25 nm, less than about 10 nm, less than about 5 nm or in ranges of about 1 nm to about 10 nm, about 5 nm to about 25 nm, about 10 nm to about 50 nm, about 25 nm to about 75 nm, about 50 nm to about 100 nm, about 75 nm to about 150 nm, about 100 nm to about 200 nm, about 150 nm to about 300 nm, about 200 nm to about 400 nm, about 300 nm to about 500 nm, about 400 nm to about 600 nm, about 500 nm to about 750 nm, about 600 nm to about 1 μm, about 750 μm to about 1.5 μm, or about 1 μm to about 2 μm. In an example, the length of the branches 150 may be less than about 500 nm, less than about 750 nm, less than about 1 μm, less than about 2 μm, less than about 3 μm, less than about 5 μm, less than about 7.5 μm, less than about 10 μm, less than about 15 μm, less than about 25 μm, less than about 50 μm, less than about 75 μm, less than about 100 μm, or in ranges of about 500 nm to about 1 μm, about 750 nm to about 1.5 μm, about 1 μm to about 2 μm, about 1.5 μm to about 3 μm, about 2 μm to about 5 μm, about 3 μm to about 7.5 μm, about 5 μm to about 10 μm, about 7.5 μm to about 15 μm, about 10 μm to about 25 μm, or about 15 μm to about 50 μm. In an embodiment, one or more of the branches 150 may branch into a plurality of additional branches.

Referring to FIG. 1C, the fibers 142 are distinct from the support 140. As such, the fibers 142 may be formed on the support 140 or formed separately from the support 140 and attached to the support 140 after forming the fibers 142. In an example, the fibers 142 may be formed via an electrospinning technique and attached to the support 140. In an example, the fibers 142 may be grown on the support 140, for instance, using a chemical vapor deposition ("CVD") or physical vapor deposition ("PVD") technique. In such an example, the support 140 may be masked prior to growing the fibers 142 on the support 140. The mask may be removed from the support 140 after growing the fibers 142 or the mask may remain. In an example, the fibers 142 may be formed using an overmolding and/or micromolding technique.

The base 104 may exhibit a different structure than the structure illustrated in FIG. 1C depending on the technique used to form the fibers 142. FIGS. 1D to 1F are cross-sectional schematics of different bases that may be used with the fluid collection assembly 100, according to different embodiments. Referring to FIG. 1D, the base 104d includes a substrate 134d that is the same or substantially similar to the substrate 134 of FIG. 1C. The base 104d also include a securement body 106d. The securement body 106d includes a support 140d and a plurality of fibers 142d. The support 140d and the fibers 142d may be the same or substantially similar to the support 140 and the fibers 142 of FIG. 1C, respectively, (e.g., formed from any of the support and/or fibers materials disclosed herein) except that the support 140d and the fibers 142d are integrally formed with each other. An example of forming the securement body 106d includes providing a piece of material. Portions of the material may be selectively removed therefrom to form the support 140d and the fibers 142d. The portion of the material may be selectively removed using a photolithography technique or any other suitable technique. It is noted that a mask may be formed on the portions of the material that form the fibers 142d to prevent the removal of such portions of the material. The masks may be removed after forming the fibers 142d.

Referring to FIG. 1E, the base 104e may include a substrate 134e and a securement body 106e attached to the substrate 134e. The securement body 106e include one or more fibers 142e that extend directly from and are distinct from the substrate 134e. In other words, at least a portion of the securement body 106e does not include a support. The fibers 142e may be formed directly on the substrate 134e in any of the same manners that the fibers 142 are formed on the support 140 of FIG. 1C. For example, preformed fibers (e.g., electro-spun fibers) may be directly attached to the substrate 134e or the fibers 142e may be grown on the substrate 134e (e.g., using CVD or PVD).

Referring to FIG. 1F, the base 104f may include a substrate 134f and a securement body 106f that are integrally formed together. For example, the securement body 106f may include a plurality of fibers 142f that are integrally formed with the substrate 134f. The base 104f may be formed by providing a piece of material and selectively removing portions of the material to form the fibers 142f. In an example, portions of the material may be removed via photolithography. In such an example, the material may be masked to prevent removal of portions of the material that form the fibers 142f. The mask may be removed after forming the fibers 142f.

Referring back to FIGS. 1A and 1B, it is noted that the securement bodies disclosed herein may be formed on at least a portion of the fluid impermeable barrier 108 instead of or in addition to the base 104. For example, the securement body formed on at least a portion of the fluid impermeable barrier 108 may include fibers attached to a support that is attached to the fluid impermeable barrier 108, integrally formed with the support that is attached to the fluid impermeable barrier 108, directly attached to the fluid impermeable barrier 108, or integrally formed with the fluid impermeable barrier 108.

As previously discussed, the fluid collection assembly 100 includes a conduit 130. The conduit 130 may be the same or substantially similar to any of the assembly tubes disclosed herein. An inlet of the conduit 130 may be located at or near the second end region 122 of the sheath 102 which is expected to be the gravimetrically low point of the chamber 114 when worn by a user. Locating the inlet of the conduit 130 at or near the second end region 122 of the sheath 102 enables the conduit 130 to receive more of the bodily fluids than if the inlet of the conduit 130 was located elsewhere and reduce the likelihood of pooling (e.g., pooling of the bodily fluids may cause microbe growth and foul odors). For instance, the bodily fluids in porous material 115 flow into the porous material 115 due to capillary forces. However, the bodily fluids may exhibit a preference to flow in the direction of gravity, especially when at least a portion of the porous material 115 is saturated with the bodily fluids. Accordingly, the inlet of the conduit 130 may be located in the fluid collection assembly 100 in a position expected to be the gravimetrically low point in the fluid collection assembly 100 when worn by a user.

In an example, the conduit 130 is configured to be at least insertable into the chamber 114, such as into the penis receiving area 128. In such an example, the conduit 130 may include one or more markers (not shown) on an exterior thereof that are located to facilitate insertion of the conduit 130 into the chamber 114. For example, the conduit 130 may include one or more markings thereon that are configured to prevent over or under insertion of the conduit 130. In another example, the conduit 130 may include one or more markings thereon that are configured to facilitate correct rotation of the conduit 130 relative to the chamber 114. The one or more markings may include a line, a dot, a sticker, or any other suitable marking.

The conduit 130 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 130 may include silicon or latex. In some examples, the conduit 130 may include one or more portions that are resilient, such as to by having one or more of a diameter or wall thickness that allows the conduit 130 to be flexible.

As described in more detail below, the conduit 130 is configured to be coupled to, and at least partially extend between, one or more of the fluid storage container (not shown) and the vacuum source (not shown). In some examples, the vacuum source may be remotely located from the fluid collection assembly 100. In such examples, the conduit 130 may be fluidly connected to the fluid storage container, which may be disposed between the vacuum source and the fluid collection assembly 100.

During operation, a male using the fluid collection assembly 100 may discharge bodily fluids (e.g., urine) into the chamber 114. The bodily fluids may pool or otherwise be collected in the chamber 114. At least some of the bodily fluids may be pulled through the interior of the conduit 130 via the inlet. The fluid may be drawn out of the fluid collection assembly 100 via the vacuum/suction provided by the vacuum source. Further examples of male fluid collection assemblies are disclosed in U.S. Provisional Patent Application No. 63/067,542 filed on Aug. 19, 2020, the disclosure of which is incorporated herein, in its entirety, by this reference.

Figure 2:
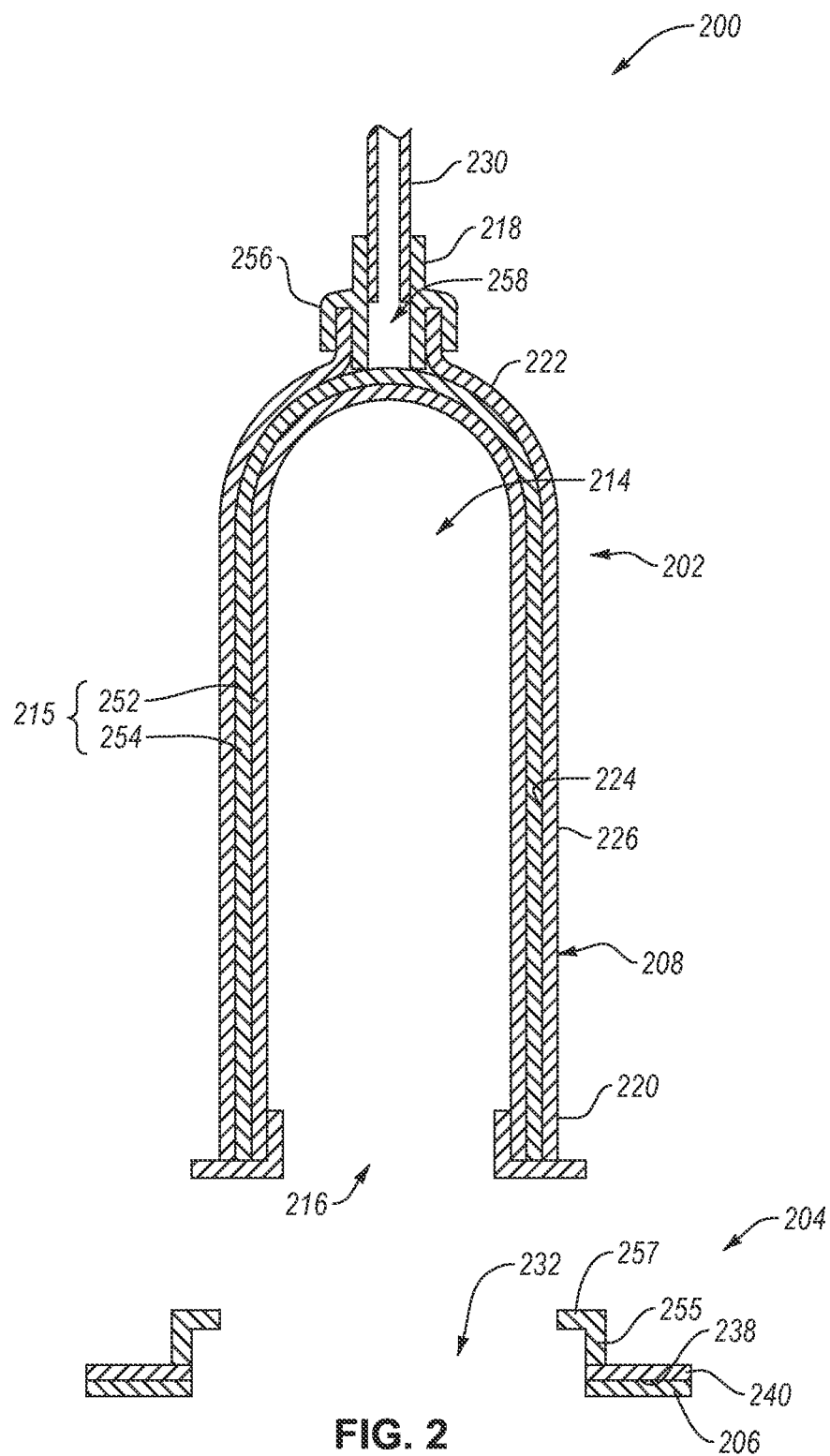
FIG. 2 is a cross-sectional schematic of a fluid collection assembly, according to an embodiment.

The securement body disclosed herein may be used with other male fluid collection assemblies. For example, FIG. 2 is a cross-sectional schematic of a fluid collection assembly 200, according to an embodiment. The fluid collection assembly 200 is a male fluid collection assembly configured to receive one or more bodily fluids from a male urethral opening. Except as otherwise disclosed herein, the fluid collection assembly 200 is the same or substantially similar to any of the fluid collection assemblies disclosed herein.

The fluid collection assembly 200 includes a sheath 202 and a base 204 and a sheath 202. The sheath 202 includes (e.g., may be formed from) a fluid impermeable barrier 208 that is sized and shaped to fit into the hollowed region of the base 204. For example, the sheath 202 may be generally tubular or cup-shaped, as shown. The generally tubular or cup-shaped fluid impermeable barrier 208 may at least partially define the outer surface 226 of the sheath 202. The fluid impermeable barrier 208 may be similar or identical to the fluid impermeable barrier 108 as disclosed herein, in one or more aspects. For example, the fluid impermeable barrier 208 may be constructed of any of the materials disclosed herein for the fluid impermeable barrier 108. The fluid impermeable barrier 208 at least partially defines the chamber 214. For example, the inner surface 224 of the fluid impermeable barrier 208 at least partially defines the perimeter of the chamber 214. The chamber 214 may be similar or identical to the chamber 114 in one or more aspects. For example, the chamber 214 may at least temporarily retain fluids therein. As shown, the fluid collection assembly 200 may include the porous material 215 therein. The porous material 215 may be similar or identical to the porous material 115 in one or more aspects. In an example, the porous material 215 may include one or more of a fluid permeable membrane 252 or a fluid permeable support 254. In an example, the porous material 215 may include any of the other porous material disclosed herein. The fluid impermeable barrier 208 may also define an opening 216 extending through the fluid impermeable barrier 208 that is configured to have a male urethra positioned therethrough.

The sheath 202 also includes at least a portion of the conduit 230 therein, such as at least partially disposed in the chamber 214. For example, the conduit 230 may extend from the sheath 202 at the second end region 222 at least partially towards a first end region 220 at least proximate to the aperture 232. The first end region 220 may be disposed near or on the skin around the male urethra (e.g., on the penis or pubic area therearound).

In some examples, the fluid impermeable barrier 208 may be constructed of a material and/or have a thickness that allows the sheath 202 to collapse when placed under vacuum, such as to remove air around a penis in the fluid collection assembly 200 during use. In such examples, the conduit 230 may extend only to or into the second end region 222 in the chamber 214 (e.g., not through to the area adjacent the opening 216). In such examples, urine may be collected and removed from the fluid collection assembly 200 at the first end region 220. It is noted that the porous material 215 may not collapse when the sheath 202 collapses thereby allowing bodily fluids to flow through the fluid collection assembly 200.

In an example, portions of the chamber 214 may be substantially empty due to the varying sizes and rigidity of the male penis. However, in some examples, the outermost regions of the chamber 214 (e.g., periphery of the interior regions of the sheath 202) may include porous material 215 (e.g., one or more of the fluid permeable membrane 252 and fluid permeable support 254). For example, the porous material 215 may be bonded to the inner surface 224 of the fluid impermeable barrier 208. The porous material 215 may be positioned (e.g., at the distal end of the chamber 214) to blunt a stream of urine from the male urethra thereby limiting splashing and/or to direct the bodily fluids to a selected region of the chamber 214. Since the chamber 214 is substantially empty (e.g., substantially all of the chamber 214 forms a reservoir), the fluids are likely to pool at a gravimetrically low point of the chamber 214. The gravimetrically low point of the chamber 214 may be at an intersection of the skin of an patient and the fluid collection assembly 200, a corner formed in the sheath 202, or another suitable location depending on the orientation of the patient.

The porous material 215 may include any of the porous material(s) disclosed herein, In an example, as previously discussed, the porous material 215 may include one or more of the fluid permeable membrane 252 or the fluid permeable support 254. One or more of the fluid permeable membrane 252 or the fluid permeable support 254 may be disposed between the fluid impermeable barrier 208 and a penis inserted into the chamber 214. The fluid permeable membrane 252 may be positioned between the fluid impermeable barrier 208 and a penis inserted into the chamber 214, such as between the fluid permeable support 254 and penis of a patient as shown. The fluid permeable support 254 may be positioned between the fluid permeable membrane 252 and the fluid impermeable barrier 208. The inner surface 224, optionally including the end of the chamber 214 substantially opposite the opening 216, may be covered with one or both the fluid permeable membrane 252 or the fluid permeable support 254. The fluid permeable support 254 or the fluid permeable membrane 252 may be affixed (e.g., adhered) to the fluid impermeable barrier 208. The fluid permeable support 254 or the fluid permeable membrane 252 may be affixed to each other. In some examples, the porous material 215 only includes the fluid permeable membrane 252 or the fluid permeable support 254.

The base 204 is sized, shaped, and made of a material to be coupled to skin that surrounds the male urethra and have the male urethra positioned therethrough. For example, the base 204 may include an substrate 234 that defines an aperture 232 in the base 204. The substrate 234 is sized and shaped to be positioned around the male urethra (e.g., positioned around and/or over the penis) and the aperture 232 may be configured to have the male urethra positioned therethrough. The substrate 234 may also be sized, shaped, made of a material, or otherwise configured to be coupled (e.g., adhesively attached, such as with a hydrogel adhesive) to the skin around the male urethra (e.g., around the penis). In an example, the substrate 234 may exhibit the general shape or contours of the skin surface that the substrate 234 is selected to be coupled with. The substrate 234 may be flexible thereby allowing the substrate 234 to conform to any shape of the skin surface. The base 204 may include a longitudinally extending flange 255 extending from the substrate 234 and a laterally extending flange 257 extending inwardly from the longitudinal extending flange 255. The longitudinally extending flange 255 and the laterally extending flange 257 define a hollowed region that is configured to receive (e.g., seal against) the sheath 202.

The base 204 also includes at least one securement body 206. For example, the securement body 206 may be attached to at least a portion of a bottom surface 238 of the substrate 234. The securement body 206 may be the same or substantially similar to any of the securement body disclosed herein. For example, the securement body 206 includes a plurality of fibers (not shown) that are configured to be attach the base 204 to a region about the urethral opening. The fibers may be attached to a support that is attached to the bottom surface 238 of the substrate 234 (as shown in FIG. 1C), integrally formed with the support (as shown in FIG. 1D), directly attached to the substrate 234 (as shown in FIG. 1E), or integrally formed with the substrate 234 (as shown in FIG. 1F).

In some examples, the fluid collection assembly 200 includes a cap 256 at a second end region 222. The cap 256 defines an interior channel through which the fluids may be removed from the fluid collection assembly 200. The interior channel is in fluid communication with the chamber 214. The cap 256 may be disposed over at least a portion of the second end region 222 of one or more of the fluid impermeable barrier 208 or the porous material 215. The cap 256 may be made of a polymer, rubber, or any other fluid impermeable material. The cap 256 may be attached to one or more of the fluid impermeable barrier 208, the porous material 215, or the conduit 130. The cap 256 may cover at least a portion of the second end region 222 of the fluid collection assembly 200. The cap 256 may laterally extend a distance from the sheath 202. The cap 256 defines a fluid outlet 218 that is sized and configured to receive and fluidly seal against the conduit 230, such as within the interior channel. The conduit 230 may extend a distance within or through the cap 256, such as to the porous material 215, through the porous material 215, or to a point set-off from the porous material 215. In the latter example, the interior channel of the cap 256 may define a reservoir 258 therein. In some examples (not shown), the cap 256 may be omitted.

The reservoir 258 is an unoccupied portion of fluid collection assembly 200 such as in the cap 256 and is void of other material. In some examples, the reservoir 258 is defined at least partially by the porous material 215 and the cap 256. During use, the fluids that are in the chamber 214 may flow through the porous material 215 to the reservoir 258. The reservoir 258 may store at least some of the fluids therein and/or position the fluids for removal by the conduit 230. In some examples, at least a portion of the porous material 215 may extend continuously between at least a portion of the opening of the interior channel and chamber 214 to wick any fluid from the opening directly to the reservoir 258.

The base 204, the sheath 202, the cap 256, and the conduit 230 may be attached together using any suitable method. For example, at least two of the base 204, the sheath 202, the cap 256, or the conduit 230 may be attached together using at least one of an interference fit, an adhesive, stitching, welding (e.g., ultrasonic welding), tape, any other suitable method, or combinations thereof.

In some examples (not shown), the fluid collection assembly 200 may have a one piece design, with one or more of the sheath 202, the base 204, and the cap 256 being a single, integrally formed piece.

Further examples of male fluid collection assemblies that may be used here are disclosed in U.S. patent application Ser. No. 16/433,773 filed on Jun. 6, 2019, the disclosure of which is incorporated herein, in its entirety, by this reference.

Figure 3A:
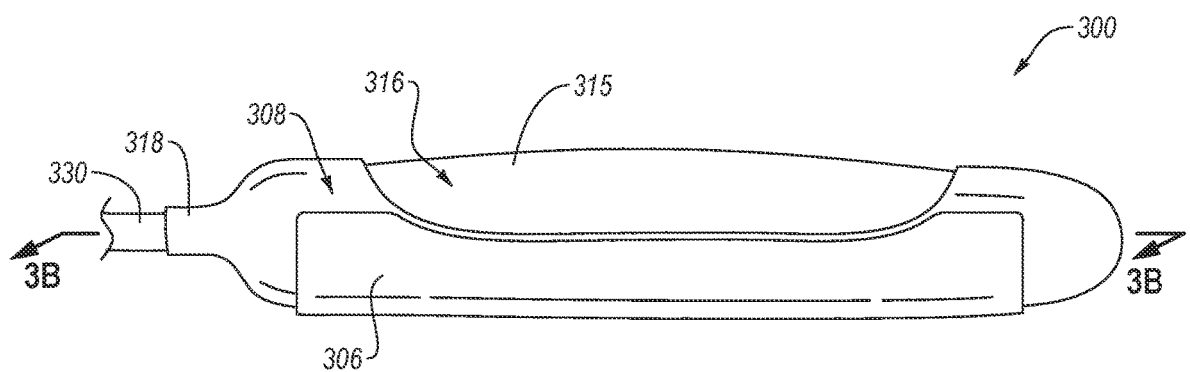
FIG. 3A is an isometric view of a fluid collection assembly, according to an embodiment.
Figure 3B:
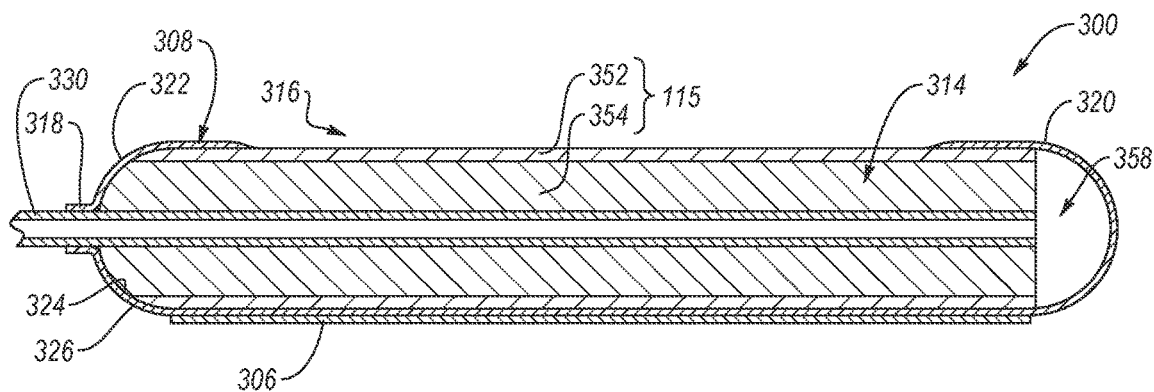
FIG. 3B is a cross-sectional schematic of the fluid collection assembly taken along plane 3B-3B shown in FIG. 3A, according to an embodiment.

The securement body disclosed herein may be used with a female fluid collection assembly. FIG. 3A is an isometric view of a fluid collection assembly 300, according to an embodiment. FIG. 3B is a cross-sectional schematic of the fluid collection assembly 300 taken along plane 3B-3B shown in FIG. 3A, according to an embodiment. The fluid collection assembly 300 is a female fluid collection assembly that is configured to be disposed adjacent to a female urethral opening. Except as otherwise disclosed herein, the fluid collection assembly 300 is the same or substantially similar to any of the fluid collection assemblies disclosed herein. The fluid collection assembly 300 includes a fluid impermeable barrier 308, at least one porous material 315 disposed in a chamber 314 defined by the fluid impermeable barrier 308, at least one securement body 306, and an optional conduit 330 at least partially disposed within the chamber 314.

The fluid impermeable barrier 308 at least partially defines a chamber 314 (e.g., interior region) and an opening 316. For example, the interior surface(s) 324 of the fluid impermeable barrier 308 at least partially defines the chamber 314 within the fluid collection assembly 300. The fluid impermeable barrier 308 temporarily stores the bodily fluids in the chamber 314. The fluid impermeable barrier 308 may be formed of any suitable fluid impermeable material(s), such as any of the fluid impermeable materials disclosed herein. As such, the fluid impermeable barrier 308 substantially prevents the bodily fluids from passing through the fluid impermeable barrier 308. In an example, the fluid impermeable barrier 308 may be air permeable and fluid impermeable. In such an example, the fluid impermeable barrier 308 may be formed of a hydrophobic material that defines a plurality of pores. At least one or more portions of at least an outer surface 326 of the fluid impermeable barrier 308 may be formed from a soft and/or smooth material, thereby reducing chaffing.

In some examples, the fluid impermeable barrier 308 may be tubular (ignoring the opening 316), such as substantially cylindrical (as shown), oblong, prismatic, or flattened tubes. During use, the outer surface 326 of the fluid impermeable barrier 308 may contact the patient. The fluid impermeable barrier 308 may be sized and shaped to fit in the gluteal cleft between the legs of a female user.

The opening 316 provides an ingress route for fluids to enter the chamber 314. The opening 316 may be defined by the fluid impermeable barrier 308 such as by an inner edge of the fluid impermeable barrier 308. For example, the opening 316 is formed in and extends through the fluid impermeable barrier 308, from the outer surface 326 to the inner surface 324, thereby enabling bodily fluids to enter the chamber 314 from outside of the fluid collection assembly 300. The opening 316 may be an elongated hole in the fluid impermeable barrier 308. For example, the opening 316 may be defined as a cut-out in the fluid impermeable barrier 308. The opening 316 may be located and shaped to be positioned adjacent to a female urethra.

The fluid collection assembly 300 may be positioned proximate to the female urethral opening and the bodily fluids may enter the chamber 314 of the fluid collection assembly 300 via the opening 316. The fluid collection assembly 300 is configured to receive the bodily fluids into the chamber 314 via the opening 316. When in use, the opening 316 may have an elongated shape that extends from a first location below the urethral opening (e.g., at or near the anus or the vaginal opening) to a second location above the urethral opening (e.g., at or near the top of the vaginal opening or the pubic hair).

The opening 316 may have an elongated shape because the space between the legs of a female is relatively small when the legs of the female are closed, thereby only permitting the flow of the bodily fluids along a path that corresponds to the elongated shape of the opening 316 (e.g., longitudinally extending opening). The opening 316 in the fluid impermeable barrier 308 may exhibit a length that is measured along the longitudinal axis of the fluid collection assembly 300 that may be at least about 20% of the length of the fluid collection assembly 300, such as about 25% to about 50%, about 40% to about 60%, about 50% to about 75%, about 65% to about 85%, or about 75% to about 95% of the length of the fluid collection assembly 300.

The opening 316 in the fluid impermeable barrier 308 may exhibit a width that is measured transverse to the longitudinal axis of the fluid collection assembly 300 that may be at least about 30% of the circumference of the fluid collection assembly 300, such as about 25% to about 50%, about 40% to about 60%, about 50% to about 75%, about 65% to about 85%, or about 75% to about 300% of the circumference of the fluid collection assembly 300. The opening 316 may exhibit a width that is greater than 50% of the circumference of the fluid collection assembly 300 since the vacuum (e.g., suction) through the conduit 330 pulls the fluid through the porous material 315 and into the conduit 330. In some examples, the opening 316 may be vertically oriented (e.g., having a major axis parallel to the longitudinal axis of the fluid collection assembly 300). In some examples (not shown), the opening 316 may be horizontally oriented (e.g., having a major axis perpendicular to the longitudinal axis of the fluid collection assembly 300). In an example, the fluid impermeable barrier 308 may be configured to be attached to the patient, such as adhesively attached (e.g., with a hydrogel adhesive) to the patient. According to an example, a suitable adhesive is a hydrogel layer.

In some examples, the fluid impermeable barrier 308 may define an fluid outlet 318 sized to receive the conduit 330. The at least one conduit 330 may be disposed in the chamber 314 via the fluid outlet 318. The fluid outlet 318 may be sized and shaped to form an at least substantially fluid tight seal against the conduit 330 or the at least one tube thereby substantially preventing the bodily fluids from escaping the chamber 314.

The fluid impermeable barrier 308 may include markings thereon, such as one or more markings to aid a user in aligning the fluid collection assembly 300 on the patient. For example, a line on the fluid impermeable barrier 308 (e.g., opposite the opening 316) may allow a healthcare professional to align the opening 316 over the urethra of the patient. In examples, the markings may include one or more of alignment guide or an orientation indicator, such as a stripe or hashes. Such markings may be positioned to align the fluid collection assembly 300 to one or more anatomical features such as a pubic bone, etc.

The fluid collection assembly 300 includes porous material 315 disposed in the chamber 314. The porous material 315 may cover at least a portion (e.g., all) of the opening 316. The porous material 315 is exposed to the environment outside of the chamber 314 through the opening 316. In an embodiment, the porous material 315 may be configured to wick any bodily fluids away from the opening 316, thereby preventing the bodily fluids from escaping the chamber 314. In an embodiment, the porous material 315 may include at least one absorbent or adsorbent material.

The porous material 315 may include any of the porous material disclosed herein. For example, the porous material 315 may include a fluid permeable membrane 352 and a fluid permeable support 354 disposed in the chamber 314. The fluid permeable membrane 352 may cover at least a portion (e.g., all) of the opening 316. The fluid permeable membrane 352 may be composed to wick the bodily fluids away from the opening 316, thereby preventing the bodily fluids from escaping the chamber 314. The fluid permeable membrane 352 may include any of the fluid permeable membrane materials disclosed herein.

The fluid permeable support 354 is configured to support the fluid permeable membrane 352 since the fluid permeable membrane 352 may be formed from a relatively foldable, flimsy, or otherwise easily deformable material. For example, the fluid permeable support 354 may be positioned such that the fluid permeable membrane 352 is disposed between the fluid permeable support 354 and the fluid impermeable barrier 308. As such, the fluid permeable support 354 may support and maintain the position of the fluid permeable membrane 352. The fluid permeable support 354 may include any material that may wick the bodily fluids, such as any of the fluid permeable membrane materials or fluid permeable support materials disclosed herein. For example, the fluid permeable membrane material(s) may be utilized in a more dense or rigid form than in the fluid permeable membrane 352 when used as the fluid permeable support 354. The fluid permeable support 354 may be formed from any fluid permeable material that is less deformable than the fluid permeable membrane 352.

In some examples, the fluid permeable membrane 352 may be optional. For example, the porous material 315 may include only the fluid permeable support 354. In some examples, the fluid permeable support 354 may be optionally omitted from the fluid collection assembly 300. For example, the porous material 315 may only include the fluid permeable membrane 352.

The fluid permeable support 354 may have a greater ability to wick the bodily fluids than the fluid permeable membrane 352, such as to move the bodily fluids inwardly from the outer surface of the fluid collection assembly 300. In some examples, the porous ability of the fluid permeable support 354 and the fluid permeable membrane 352 may be substantially the same.

The fluid permeable membrane 352 and the fluid permeable support 354 may at least substantially completely fill the portions of the chamber 314 that are not occupied by the conduit 330. In some examples, the fluid permeable membrane 352 and the fluid permeable support 354 may not substantially completely fill the portions of the chamber 314 that are not occupied by the conduit 330. In such an example, the fluid collection assembly 300 includes the reservoir 358 disposed in the chamber 314.

The reservoir 358 is a substantially unoccupied portion of the chamber 314. The reservoir 358 may be defined between the fluid impermeable barrier 308 and one or both of the fluid permeable membrane 352 and fluid permeable support 354. The bodily fluids that are in the chamber 314 may flow through the porous material 315 to the reservoir 358. The fluid impermeable barrier 308 may retain the bodily fluids in the reservoir 358. While depicted in the first end region 320, the reservoir 358 may be located in any portion of the chamber 314 such as the second end region 322. The reservoir 358 may be located in a portion of the chamber 314 that is designed to be located in a gravimetrically low point of the fluid collection assembly when the fluid collection assembly is worn.

In some examples (not shown), the fluid collection assembly 300 may include multiple reservoirs, such as a first reservoir that is located at the portion of the chamber 314 closest to the inlet of the conduit 330 (e.g., first end region 320) and a second reservoir that is located at the portion of the of the chamber 314 that is at or near second end region 322). In another example, the fluid permeable support 354 is spaced from at least a portion of the conduit 330, and the reservoir 358 may be the space between the fluid permeable support 354 and the conduit 330.

The conduit 330 may be at least partially disposed in the chamber 314. The conduit 330 may be used to remove the bodily fluids from the chamber 314. The conduit 330 (e.g., a tube) includes an inlet of the conduit 330 and an outlet 312 positioned downstream from the inlet of the conduit 330.

The outlet 312 may be operably coupled to a suction source, such as a vacuum pump for withdrawing fluid from the chamber 314 through the conduit 330. For example, the conduit 330 may extend into the fluid impermeable barrier 308 from the second end region 322 and may extend to the first end region 320 to a point proximate to the reservoir 358 therein such that the inlet of the conduit 330 is in fluid communication with the reservoir 358. The conduit 330 fluidly couples the chamber 314 with the fluid storage container (not shown) or the vacuum source (not shown).

The conduit 330 may extend through a bore in the fluid permeable membrane 352 and/or fluid permeable support 354, such as into the reservoir 358. For example, the inlet of the conduit 330 may be extend into or be positioned in the reservoir 358. In the illustrated embodiment, the conduit 330 is at least partially disposed in the reservoir 358. In some examples (not shown), the conduit 330 may enter the chamber 314 in the distal end region and the inlet of the conduit 330 of the conduit 330 may be disposed in the distal end region (e.g., in the reservoir 358). The bodily fluids collected in the fluid collection assembly 300 may be removed from the chamber 314 via the conduit 330.

In some examples, the inlet of the conduit 330 may not extend into the reservoir 358. In such examples, the inlet of the conduit 330 may be disposed within the porous material 315 (fluid permeable membrane 352 and/or fluid permeable support 354) or at a terminal end thereof. For example, an end of the conduit 330 may be coextensive with or recessed within the fluid permeable membrane 352 and/or fluid permeable support 354.

During use, the first end region 320 may be the gravimetrically low point of the chamber 314. As such, locating the inlet of the conduit 330 at or near a location expected to be the gravimetrically low point of the chamber 314 when worn by a patient enables the conduit 330 to receive more of the bodily fluids than if inlet of the conduit 330 was located elsewhere and reduce the likelihood of pooling (e.g., pooling of the bodily fluids may cause microbe growth and foul odors). For instance, as previously discussed, the bodily fluids in the fluid permeable membrane 352 and the fluid permeable support 354 may flow in any direction due to capillary forces. However, the bodily fluids may exhibit a preference to flow in the direction of gravity, especially when at least a portion of the fluid permeable membrane 352 and/or the fluid permeable support 354 is saturated with the bodily fluids. Accordingly, one or more of the inlet of the conduit 330 or the reservoir 358 may be located in the fluid collection assembly 300 in a position expected to be the gravimetrically low point in the fluid collection assembly 300 when worn by a patient, such as the first end region 320.

As previously discussed, the fluid collection assembly 300 may include at least one securement body 306. The securement body 306 may be configured to be attached to the skin of the patient, such as at least one of the thighs or the region about the urethral opening. As such, the securement body 206 may be attached to or formed on at least a portion of an outer surface 326 of the fluid impermeable barrier 308 that, during use, may contact the skin of the patient. The securement body 306 may be the same or substantially similar to any of the securement body disclosed herein. As such, the securement body 306 includes a plurality of fibers that are configured to be attach the securement body to the skin of a patient.

In an embodiment, the securement body 306 is distinct from the fluid impermeable barrier 308. In such an embodiment, the securement body 306 may include at least one of a plurality of fibers attached to or integrally formed with a support, similar to what is shown in FIGS. 1C and 1D, respectively. In such an embodiment, the support may be attached to the fluid impermeable barrier 308 using any suitable technique, such as with a chemical adhesive, a dry adhesive, etc. in an embodiment, the securement body 306 may include a plurality of fibers at least one of attached directly to the fluid impermeable barrier 308 or integrally formed with the fluid impermeable barrier 308, similar to what is shown in FIGS. 1E and 1F, respectively.

Other embodiments of fluid impermeable barriers, fluid permeable membranes, fluid permeable supports, chambers, and their shapes and configurations are disclosed in U.S. Pat. No. 10,973,678 filed on Jun. 2, 2017; U.S. Pat. No. 10,390,989 filed on Sep. 8, 2016; and U.S. Pat. No. 10,226,376 filed on Jun. 3, 2017, the disclosure of each of which is incorporated herein, in its entirety, by this reference.

Figure 4A:
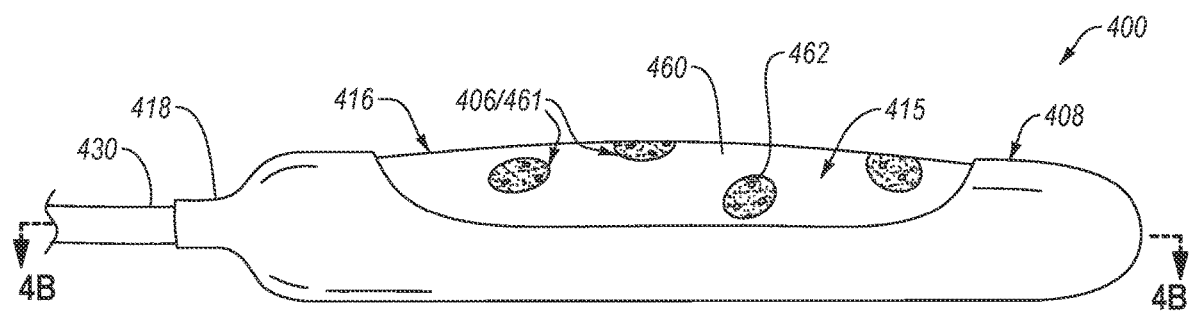
FIG. 4A is an isometric view of a fluid collection assembly that includes at least one friction material, according to an embodiment.
Figure 4B:
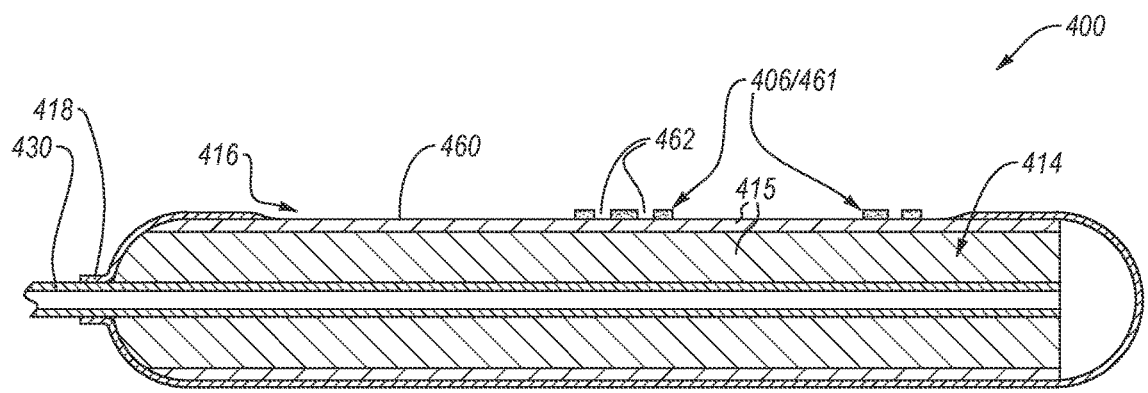
FIG. 4B is a cross-sectional schematic of the fluid collection assembly taken along plane 4B-4B shown in FIG. 4A, according to an embodiment.

The securement body illustrated in FIGS. 1A-3B include a plurality of fibers. However, the securement body may include one or more additional types of securement bodies, such at least one friction material, instead of or in addition to the securement bodies illustrated in FIGS. 1A-3B. For example, FIG. 4A is an isometric view of a fluid collection assembly 400 that includes at least one friction material 461, according to an embodiment. FIG. 4B is a cross-sectional schematic of the fluid collection assembly 400 taken along plane 4B-4B shown in FIG. 4A, according to an embodiment. The fluid collection assembly 400 is an example of a female fluid collection assembly. As such, except as otherwise disclosed herein, the fluid collection assembly 400 may be the same or substantially similar to the fluid collection assembly 300 shown in FIGS. 3A and 3B. For example, the fluid collection assembly 400 may include a fluid impermeable barrier 408 that defines a chamber 414, at least one opening 416, and a fluid outlet 418. The fluid collection assembly 400 may include at least one porous material 415 disposed in the chamber 414 and an optional conduit 430. Except as otherwise disclosed herein, the fluid impermeable barrier 408, the porous material 415, and the conduit 430 may be the same or substantially similar to any of the fluid impermeable barriers, porous materials, and conduits, respectively, disclosed herein.

The porous material 415 includes a contact surface 460 that is configured to contact the patient during use. The contact surface 460 may include the portion of the porous material 415 that extends across the opening 416.

The fluid collection 400 includes at least one securement body 406. The securement body 406 includes at least one friction material 461 disposed on at least a portion of the contact surface 460. The contact surface 460 exhibits a first coefficient of friction and the friction material 461 exhibits a second coefficient of friction that is greater than the first coefficient of friction. As such, the friction material 461 better prevents movement of the fluid collection assembly 400 when the opening is adjacent to the region about the urethral opening of the patient than if the fluid collection assembly 400 did not include the friction material 461. In is noted that, as used herein, the coefficient of friction refers to the coefficient of static friction of the material (e.g., the contact surface 460 or the friction material 461) against the against the skin of the patient when the skin is at least one of dry or moist.

The friction material 461 includes a material disposed on the contact surface 460 of the porous material 415. The material of the friction material 461 is different than the material that forms the porous material 415 which, at least in part, causes the friction material 461 to exhibit a coefficient of friction that is greater than the contact surface 460.

In an example, the friction material 461 includes at least one elastomer, such as at least one of silicone, nitrile, rubber, neoprene, or another elastomer.

The friction material 461 may be disposed on the contact surface 460 using any suitable technique. In an example, the friction material 461 may include an adhesive on the surface of the friction material 461 that contacts the contact surface 460. In an example, the surface of the friction material 461 that contacts the contact surface 460 may be partially melted and the friction material 461 may be pressed into the contact surface 460. At least some of the melted portions of the friction material 461 may flow into and at least partially occupy some of the pores of the porous material 415 thereby attaching the friction material 461 to the porous material 415. In an example, the friction material 461 may be applied to the contact surface 460 while in a melted (e.g., liquid) state. Some of the melted friction material 461 may flow into and at least partially occupy some of the pores of the porous material 415 thereby attaching the friction material 461 to the porous material 415.

As previously discussed, the friction material 461 is disposed on the contact surface 460 of the porous material 415. As such, the friction material 461 may block portions of the porous material 415 that extend across the opening 416. In some embodiments, blocking portions of the porous material 415 that extend across the opening 416 may at least one of limit the amount of bodily fluids that may enter the chamber (not shown) or cause the bodily fluids to splash, either or which may cause bodily fluids to leak or otherwise inhibit the functionality of the fluid collection assembly 400. However, the friction material's 461 the ability to better maintain the position of the fluid collection assembly 400 against the region about the urethral opening still decreases the likelihood that the bodily fluids leak even though the friction material 461 may obstruct portions of the porous material 415 and cause splashing.

In an embodiment, the friction material 461 may define one or more passageways 462 (e.g., pores, voids, etc.) extending therethrough. The passageways 462 allow the bodily fluids to flow through the friction material 461 to the contact surface 460 of the porous material 415 and decrease splashing of the bodily fluids. Thus, the passageways 462 may further prevent bodily fluids from leaking from the fluid collection assembly 400. The passageways 462 may be formed using any suitable technique. In an example, the friction material 461 may be applied to the contact surface 460 in a manner that causes peaks and valleys to form and at least some of the valleys form the passageways 462. In an example, the friction material 461 may include one or more cutouts formed therein either before or after applying the friction material 461 to the contact surface 460. The cutouts may form the passageways 462. In an example, the friction material 461 may include a plurality of pores (e.g., interconnected pores) that form the passageways 462.

The friction material 461 illustrated in FIGS. 4A and 4B are in the form of dots. The friction material 461 are in the form of dots when at least some of the friction material 461 are completely laterally surrounded by the porous material 415. Optionally, some of the friction material 461 may be on the boundary between the fluid impermeable barrier 408 and the contact surface 460 and such friction material 461 are collectively completely laterally surrounded by the porous material 415 and the fluid impermeable barrier 408. Forming the friction material 461 as dots may allow for selective placement of the friction material 461, such as to avoid the urethral opening or increase the likelihood that the friction material 461 contacts skin. Further, forming the friction material 461 as dots may decrease the surface area of the contact surface 460 that the friction material 461 covers thereby decreasing the likelihood that the friction material 461 obstructs fluid flow or causes splashing.

Figure 4C:
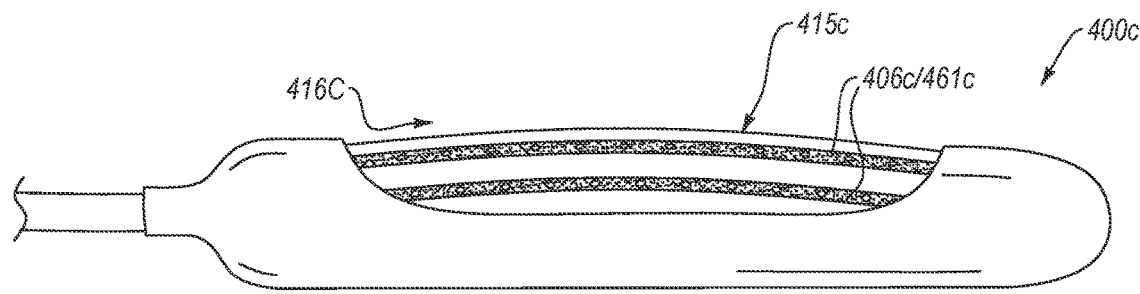
FIGS. 4C-4E are isometric views of different fluid collection assemblies that include the friction material disposed therein in different arrangements, according to different embodiments.
Figure 4D:
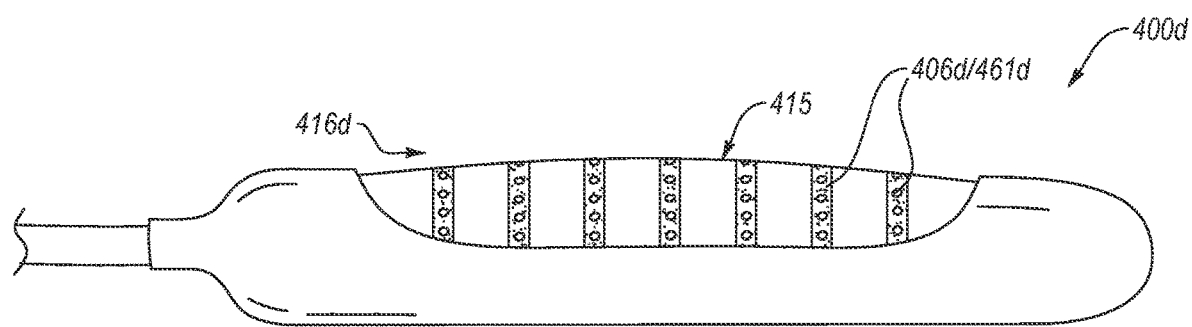
Figure 4E:
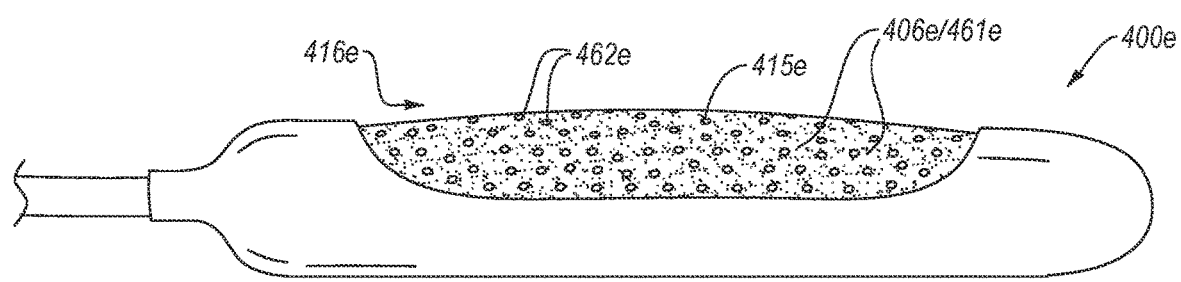

The friction material 461 does not have to be arranged on the porous material 415 in the form of dots. For example, FIGS. 4C-4E are isometric views of different fluid collection assemblies that include the friction material disposed therein in different arrangements, according to different embodiments. Except as otherwise disclosed herein, the fluid collection assemblies illustrated in FIGS. 4C-4E are the same or substantially similar to any of the fluid collection assemblies disclosed herein.

Referring to FIG. 4C, the fluid collection assembly 400c includes a porous material 415c extending across at least one opening 416c and at least one securement body 406c. The securement body 406c includes at least one friction material 461d disposed on the porous material 415c. The friction material 461 is arranged as one or more longitudinally extending strips that extend generally parallel to a longitudinal axis of the fluid collection assembly 400c. The strips are more likely to contact anatomical features that extend obliquely or perpendicularly relative to a longitudinal axis of the of the fluid collection assembly 400c, such as the clitoral head, the mons pubis, and the perineum. The strips may also contact a greater percentage of anatomical features that generally extend parallel to the longitudinal axis of the fluid collection assembly 400c, such as the labia folds, if correctly positioned (e.g., the space between the strips are not spaced directly over the labia folds).

Referring to FIG. 4D, the fluid collection assembly 400d includes a porous material 415d extending across at least one opening 416d and at least one securement body 406d. The securement body 406d includes at least one friction material 461d disposed on the porous material 415d. The friction material 461d is arranged as one or more longitudinally extending strips that extend generally perpendicular to a longitudinal axis of the fluid collection assembly 400c. The strips are more likely to contact anatomical features that extend obliquely or parallel to a longitudinal axis of the of the fluid collection assembly 400c, such as the labia folds. For example, the strips illustrated in FIG. 4D are more likely to contact the labia folds than the strips illustrated in FIG. 4C regardless of the position of the fluid collection assemblies thereof. However, the strip illustrated in FIG. 4C may contact a greater percentage of the labia folds if the strips are disposed directly over the labia folds than the strips illustrated in FIG. 4D.

Referring to FIG. 4E, the fluid collection assembly 400e includes a porous material 415e extending across at least one opening 416e and at least one securement body 406e. The securement body 406e includes at least one friction material 461e disposed on the porous material 415e. The friction material 461e may be disposed on the porous material 415e to cover substantially all of the porous material. As such, the friction material 461e is more likely to contact skin and to contact a greater quantity of skin that the friction material illustrated in FIGS. 4A-4D. However, the friction material 461e must define one or more passageways 462e therethrough to allow the bodily fluids to flow into the chamber thereof (not shown).

It is noted that the arrangement of the friction material illustrated in FIGS. 4A-4E are provided for illustrative purposes only and that the friction material disclosed herein may exhibit different arrangements. In an example, the friction material may be arranged in strips that extend obliquely relatively to the longitudinal axis of the fluid collection assembly. In an example, the friction material may be arranged in the form of one or more dashed lines. In an example, the friction material may be arranged in a curved line. In an example, the friction material may be arranged in a combination of any of the arrangements disclosed herein (e.g., a checkered arrangement that includes a plurality of strips that extend parallel to and perpendicular to a longitudinal axis of the fluid collection assembly).

The friction materials disclosed above include the friction materials disposed on the porous material of female fluid collection assemblies. However, it is noted that the friction materials disclosed herein may be disposed on the porous materials of any of the male fluid collection assemblies disclose herein. Such friction materials may help maintain the penis in the chambers of such male fluid collection assemblies when the penis would otherwise become buried thereby preventing or minimizing pooling of bodily fluids caused by buried penises. The arrangement of the friction material on the porous materials of the male fluid collection assemblies may be the same or substantially similar to the arrangement of any of the friction material disclosed above with regards to the female fluid collection assemblies.

Figure 5A:
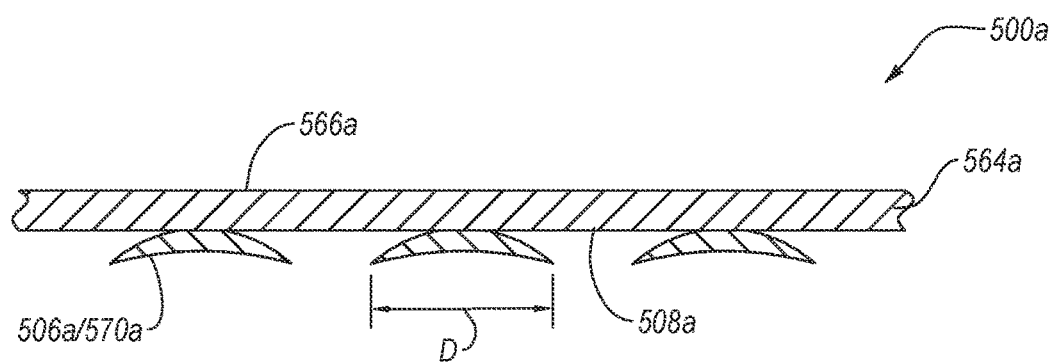
FIG. 5A is a cross-sectional schematic of a portion of a fluid collection assembly, according to an embodiment.

The fluid collection assemblies disclosed herein may include securement body instead of or in addition to the fibers and the friction materials disclosed above. For example, FIG. 5A is a cross-sectional schematic of a portion of a fluid collection assembly 500a, according to an embodiment. The fluid collection assembly 500a includes a base layer 564a. The base layer 564a may be, for example, a fluid impermeable layer, porous material, or a substrate of a base. The base layer 564a includes a top surface 566a and a bottom surface 568a. The bottom surface 568a is configured to be closer to a patient (e.g., adjacent to the skin of the patient) than the top surface 566a during use.

The fluid collection assembly 500a includes at least one securement body 506a. The securement body 506a include one or more suction cups 570a directly attached to or integrally formed with the base layer 564a. In particular, the suction cups 570a extend from the bottom surface 568a of the base layer 564a. The suction cups 570a are formed from a flexible material that is impermeable to air, such as nitrile, neoprene, polyurethane, silicone, rubber, vinyl, any other suitable polymer, or combinations thereof. The suction cups 570a may exhibit any concave shape. For example, the suction cups 570a may exhibit a conical or other cup-like shape having, for example, a circular or oblong opening.

The suction cups 570a may exhibit a maximum lateral dimension D (e.g., diameter). The maximum lateral dimension D of the suction cups 570a may be selected to be about 1 mm to about 3 mm, about 2 mm to about 4 mm, about 3 mm to about 5 mm, about 4 mm to about 6 mm, about 5 mm to about 7 mm, about 6 mm to about 8 mm, about 7 mm to about 9 mm, about 8 mm to about 1 cm, about 9 mm to about 1.2 cm, about 1 cm to about 1.4 cm, about 1.2 cm to about 1.6 cm, about 1.4 cm to about 1.8 cm, about 1.6 cm to about 2 cm, about 1.8 cm to about 2.25 cm, about 2 cm to about 2.5 cm, about 2.25 cm to about 2.75 cm, about 2.5 cm to about 3 cm, about 2.75 cm to about 3.5 cm, or about 3 cm to about 4 cm. The maximum lateral dimension D of the suction cups 570a may be selected based on a number of factors. Generally, the maximum lateral dimension D may be selected based on two competing factors, namely increasing the force required to detach the suction cups 570a and minimizing hickies and general discomfort caused by the suction cups 570a. For example, generally increasing the lateral dimension D may increase the force required to detach the suction cups 570a but also increases the likelihood of hickies and/or patient discomfort, especially if the fluid collection assembly 500a is used for a prolonged period of time. However, decreasing the maximum lateral dimension D may allow the fluid collection assembly 500a to include more suction cups 570a which may at least partially offset the decrease force required to detach the suction cups 570a.

Figure 5B:
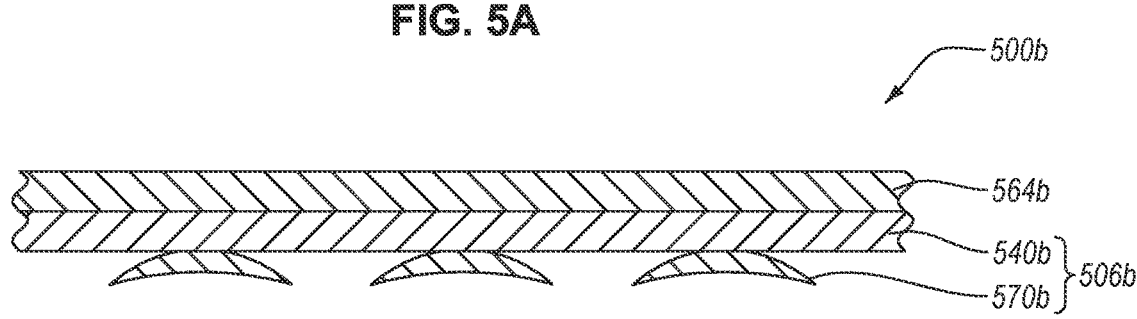
FIG. 5B is a cross-sectional schematic of a portion of a fluid collection assembly, according to an embodiment.

FIG. 5B is a cross-sectional schematic of a portion of a fluid collection assembly 500b, according to an embodiment. Except as otherwise disclosed herein, the fluid collection assembly 500b is the same or substantially similar to the fluid collection assembly 500a. For example, the fluid collection assembly 500b may include a base layer 564b and at least one securement body 506b. However, the securement body 506b may include a support 540b and a plurality of suction cups 570b extending from the support 540b. The support 540b may the the same or substantially similar to the support 140 illustrated in FIG. 1C. The support 540b may facilitate manufacture of the base layer 564b. For example, the base layer 564b may be manufactured using traditional methods (e.g., extrusion, tape casting, etc.) instead of other techniques that are required to form the base layer 564b with the suction cups 570b directly disposed therein.

Figure 6:
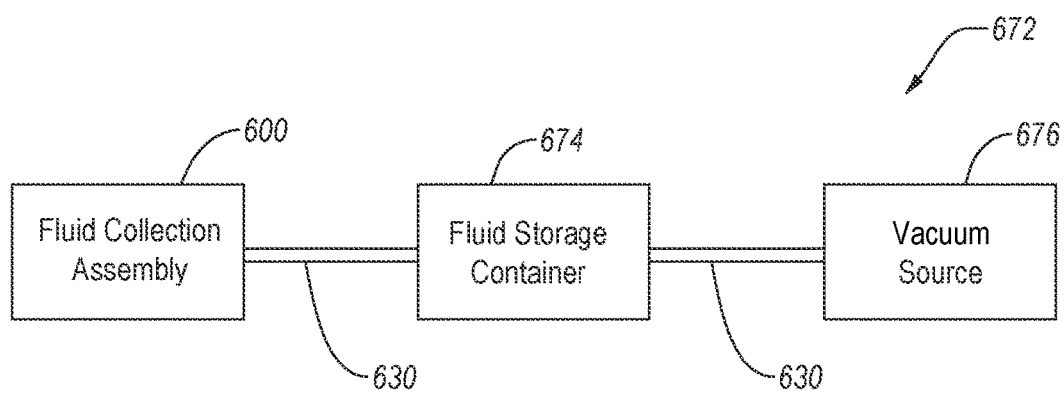
FIG. 6 is a block diagram of a system for fluid collection, according to an embodiment.

FIG. 6 is a block diagram of a system 672 for fluid collection, according to an embodiment. The system 672 includes a fluid collection assembly 600, a fluid storage container 674, and a vacuum source 676. The fluid collection assembly 600, the fluid storage container 674, and the vacuum source 676 may be fluidly coupled to each other via one or more conduits 630. For example, fluid collection assembly 600 may be operably coupled to one or more of the fluid storage container 674 or the vacuum source 676 via the conduit 630. Bodily fluids (e.g., urine or other bodily fluids) collected in the fluid collection assembly 600 may be removed from the fluid collection assembly 600 via the conduit 630 which protrudes into the fluid collection assembly 600. For example, an inlet of the conduit 630 may extend into the fluid collection assembly 600, such as to a reservoir therein. The outlet of the conduit 630 may extend into the fluid storage container 674 or the vacuum source 676. Suction force may be introduced into the chamber of the fluid collection assembly 600 via the inlet of the conduit 630 responsive to suction (e.g., vacuum) force applied at the outlet of the conduit 630.

The suction force may be applied to the outlet of the conduit 630 by the vacuum source 676 either directly or indirectly. The suction force may be applied indirectly via the fluid storage container 674. For example, the outlet of the conduit 630 may be disposed within the fluid storage container 674 and an additional conduit 630 may extend from the fluid storage container 674 to the vacuum source 676. Accordingly, the vacuum source 676 may apply suction to the fluid collection assembly 600 via the fluid storage container 674. The suction force may be applied directly via the vacuum source 676. For example, the outlet of the conduit 630 may be disposed within the vacuum source 676. An additional conduit 630 may extend from the vacuum source 676 to a point outside of the fluid collection assembly 600, such as to the fluid storage container 674. In such examples, the vacuum source 676 may be disposed between the fluid collection assembly 600 and the fluid storage container 674.

The fluid collection assembly 600 may be similar or identical to any of the fluid collection assemblies disclosed herein in one or more aspects. The fluid collection assembly 600 may be shaped and sized to be positioned adjacent to a female urethral opening or have a male urethral opening positioned therethrough (e.g., receive a penis therein). For example, the fluid collection assembly 600 may include a fluid impermeable barrier at least partially defining a chamber (e.g., interior region) of the fluid collection assembly 600. The fluid impermeable barrier also defines at least one opening extending therethrough from the external environment. The opening may be positioned adjacent to a female urethral opening or have a male urethral opening positioned therethrough. The fluid collection assembly 600 may include porous material disposed in the chamber such as one or more of a fluid permeable support and a fluid permeable membrane. The fluid collection assembly 600 includes one or more of any of the securement bodies disclosed herein.

The fluid storage container 674 is sized and shaped to retain the bodily fluids therein. The fluid storage container 674 may include a bag (e.g., drainage bag), a bottle or cup (e.g., collection jar), or any other enclosed container for storing bodily fluids such as urine. In some examples, the conduit 630 may extend from the fluid collection assembly 600 and attach to the fluid storage container 674 at a first point therein. An additional conduit 630 may attach to the fluid storage container 674 at a second point thereon and may extend and attach to the vacuum source 676. Accordingly, a vacuum (e.g., suction) may be drawn through fluid collection assembly 600 via the fluid storage container 674. Fluid, such as urine, may be drained from the fluid collection assembly 600 using the vacuum source 676.

The vacuum source 676 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 676 may provide a vacuum or suction to remove fluid from the fluid collection assembly 600. In some examples, the vacuum source 676 may be powered by one or more of a power cord (e.g., connected to a power socket), one or more batteries, or even manual power (e.g., a hand operated vacuum pump). In some examples, the vacuum source 676 may be sized and shaped to fit outside of, on, or within the fluid collection assembly 600. For example, the vacuum source 676 may include one or more miniaturized pumps or one or more micro pumps. The vacuum sources 676 disclosed herein may include one or more of a switch, a button, a plug, a remote, or any other device suitable to activate the vacuum source 676.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:

1. A fluid collection assembly, comprising: a fluid impermeable barrier at least defining a chamber, at least one opening, and a fluid outlet; at least one porous material disposed in the chamber; and at least one securement body configured to limit movement of the fluid collection assembly relative to a region about a urethral opening of a patient, the at least one securement body including: a plurality of fibers exhibiting an average lateral dimension of about 5 μm or less, the plurality of fibers extend from at least one exterior surface of the fluid collection assembly, at least most of the plurality of fibers extend from the at least one exterior surface at an average angle that is oblique relative to the at least one exterior surface, the at least one securement body further including a plurality of branches extending from or attached to at least some of the plurality of fibers, at least some of the plurality of branches exhibiting an average diameter of 300 nm to 2 μm, one or more of the plurality of branches extending from or attached to a portion of one of the plurality of fibers that is spaced from a terminal end of the one of the plurality of fibers, wherein the terminal end of the one of the plurality of fibers is an end of the one of the plurality of fibers farthest spaced from the at least one exterior surface.

2. The fluid collection assembly of claim 1, further comprising a base and a sheath, the base including a substrate having a top surface and a bottom surface opposite the top surface, the top surface attached to one or more other components of the fluid collection assembly, the bottom surface attached to the at least one securement body.

3. The fluid collection assembly of claim 1, wherein the at least one securement body is attached to or integrally formed with at least a portion of a surface of the fluid impermeable barrier that is opposite the at least one opening.

4. The fluid collection assembly of claim 1, wherein the at least one securement body includes a support attached to one or more components of the fluid collection assembly, the plurality of fibers extending from the support.

5. The fluid collection assembly of claim 1, wherein the plurality of fibers are directly attached to one of: at least one outer surface of the fluid impermeable barrier, wherein the at least one outer surface is opposite a surface of the fluid impermeable barrier that defines the chamber; or a bottom surface of a base, wherein the base includes a top surface opposite the bottom surface, a portion of the top surface attached to a sheath, the sheath including the fluid impermeable barrier.

6. The fluid collection assembly of claim 1, wherein the plurality of fibers are integrally formed with one of: at least one outer surface of the fluid impermeable barrier, wherein the at least one outer surface is opposite a surface of the fluid impermeable barrier that defines the chamber; or a bottom surface of a base, wherein the base includes a top surface opposite the bottom surface, a portion of the top surface attached to a sheath, the sheath including the fluid impermeable barrier.

7. The fluid collection assembly of claim 1, wherein the average angle is less than 45°.

8. The fluid collection assembly of claim 1, wherein the at least one securement body includes a support attached to and distinct from a substrate, the plurality of fibers attached to or integrally formed with the support.

9. The fluid collection assembly of claim 1, wherein: the at least one opening includes an elongated opening configured to be positioned adjacent to female anatomy; the at least one porous material extends across the elongated opening; and the at least one securement body is positioned adjacent at least to portions of the fluid impermeable barrier defining the elongated opening, at least the portion of the at least one securement body adjacent to the elongated opening including the plurality of fibers.

10. The fluid collection assembly of claim 2, wherein: the at least one opening includes an elongated opening configured to be positioned adjacent to female anatomy; the at least one porous material extends across the elongated opening; and the at least one securement body is positioned adjacent at least to portions of the fluid impermeable barrier opposite the elongated opening, at least the portion of the at least one securement body opposite the elongated opening including the plurality of fibers.

11. The fluid collection assembly of claim 1, wherein at least some of the plurality of branches exhibit an average diameter of 500 nm to 2 μm.

12. A fluid collection system, comprising: a fluid storage container configured to hold one or more bodily fluids therein; a fluid collection assembly including: a fluid impermeable barrier at least defining a chamber, at least one opening, and a fluid outlet; at least one porous material disposed in the chamber; and at least one securement body configured to limit movement of the fluid collection assembly relative to a region about a urethral opening of a patient, the at least one securement body including: a plurality of fibers exhibiting an average lateral dimension of about 5 μm or less, the plurality of fibers extend from at least one exterior surface of the fluid collection assembly, at least most of the plurality of fibers extend from the at least one exterior surface at an average angle that is oblique relative to the at least one exterior surface, the at least one securement body further including a plurality of branches extending from or attached to at least some of the plurality of fibers, at least some of the plurality of branches exhibiting an average diameter of 300 nm to 2 μm, one or more of the plurality of branches extending from or attached to a portion of one of the plurality of fibers that is spaced from a terminal end of the one of the plurality of fibers, wherein the terminal end of the one of the plurality of fibers is an end of the one of the plurality of fibers farthest spaced from the at least one exterior surface; and a vacuum source in fluid communication with the fluid storage container and the fluid collection assembly, the vacuum source configured to draw the one or more bodily fluids from the fluid collection assembly and deposit the one or more bodily fluids in the fluid storage container via one or more conduits.

* * * * *